United States Patent
Yuthavong et al.

(10) Patent No.: US 8,530,491 B2
(45) Date of Patent: Sep. 10, 2013

(54) ANTIMALARIAL COMPOUNDS WITH FLEXIBLE SIDE-CHAINS

(75) Inventors: Yongyuth Yuthavong, Klong Luang (TH); Tirayut Vilaivan, Patumwan (TH); Sumalee Kamchonwongpaisan, Klong Luang (TH); Bongkoch Tarnchompoo, Klong Luang (TH); Chawanee Thongpanchang, Klong Luang (TH); Penchit Chitnumsub, Klong Luang (TH); Jirundon Yuvaniyama, Ratchathewi (TH); David Matthews, Encinitas, CA (US); William Charman, Parkville (AU); Susan Charman, Parkville (AU); Livia Vivas, Keppel (GB); Sanjay Babu Katiyar, Salt Lake (IN)

(73) Assignee: Medicines for Malaria Venture (MMV), Geneva (CH)

( * ) Notice: Subject to any disclaimer, the term of this patent is extended or adjusted under 35 U.S.C. 154(b) by 841 days.

(21) Appl. No.: 12/247,953

(22) Filed: Oct. 8, 2008

(65) Prior Publication Data

US 2009/0099220 A1   Apr. 16, 2009

Related U.S. Application Data

(60) Provisional application No. 60/978,375, filed on Oct. 8, 2007.

(51) Int. Cl.
*A61K 31/505* (2006.01)
*C07D 401/02* (2006.01)

(52) U.S. Cl.
USPC ............................ 514/275; 544/323; 544/324

(58) Field of Classification Search
USPC .................................. 514/275; 544/323, 324
See application file for complete search history.

(56) References Cited

U.S. PATENT DOCUMENTS

| | | | |
|---|---|---|---|
| 4,033,962 A | 7/1977 | Rosen | |
| 4,179,562 A | 12/1979 | Ponsford | |
| 4,232,023 A | 11/1980 | Dick et al. | |
| 5,521,192 A * | 5/1996 | Henrie et al. ................ | 514/275 |
| 7,371,758 B2 | 5/2008 | Yuthavong et al. | |

FOREIGN PATENT DOCUMENTS

| | | |
|---|---|---|
| EP | 1 180 369 A1 | 2/2002 |
| GB | 2 086 386 A | 5/1982 |
| WO | WO 94/12032 A1 | 6/1994 |

OTHER PUBLICATIONS

Bowden et al., Structure-activity relations. Part 8. Some novel designed 2,4-diaminopyrimidine inhibitors of dihydrofolic acid reductase; Journal of Chemical Research, Synopses (1991), (7), 184-5.*

International Search Report and Written Opinion mailed Dec. 11, 2008, for PCT Application No. PCT/US08/79210 filed Oct. 8, 2008, 8 pages.

Bowden, K., et al., "Interactions between inhibitors of dihydrofolate reductase,"Biochemical Journal, The biochemical Society, GB, vol. 258, No. 2, Jan. 1, 1989, pp. 335-342, XP008146435, ISSN: 0306-3275.

Bowden, Keith, et al., "Structure-activity relations. Part 8. Some novel designed 2,4-diaminopyridine inhibitors of diydrofolic acid reductase," Journal of Chemical Research, Science Reviews Ltd, GB, No. 7, Jan. 1, 1991, pp. 184-185, XP008146434, ISSN: 0308-2342.

Hill, J., "The activity of drug combinations against established infections of rodent malaria," Parasitology, Cambridge University Press, London, GB, vol. 95, No. 1, Jan. 1, 1987, pp. 17-23, XP008146418, ISSN: 0031-1820.

* cited by examiner

*Primary Examiner* — James O Wilson
*Assistant Examiner* — Ebenezer O Sackey
(74) *Attorney, Agent, or Firm* — Faegre Baker Daniels LLP

(57) ABSTRACT

The present invention relates to novel compounds that are inhibitors of wild type and mutant dihydrofolate reductase (DHFR) of *Plasmodium falciparum*, which are useful for the treatment of malaria. It also relates to processes of making and using such compounds. The antimalarial compounds of the present invention have low toxicity to a host infected with the malarial parasite, and are potent when administered in pharmaceutical compositions.

36 Claims, 9 Drawing Sheets

R = H, Et

R = H, Et

R = H, Et

ANTIMALARIAL COMPOUNDS WITH FLEXIBLE SIDE-CHAINS

CROSS-REFERENCE TO RELATED APPLICATIONS

This application claims the benefit of U.S. Provisional Application No. 60/978,375, filed on Oct. 8, 2007.

FIELD OF THE INVENTION

The present invention relates to antimalarial compounds or antifolates for the treatment of malaria and methods of making and using the compounds.

BACKGROUND OF THE INVENTION

Malaria is a mosquito-borne disease that causes over 2.7 million deaths per year according to estimates by the World Health Organization (WHO). Malaria is a potentially fatal blood disease caused by a parasite that is transmitted to human and animal hosts by the *Anopheles* mosquito. There are four human parasites including *Plasmodium falciparum* (*P. falciparum*), *Plasmodium vivax* (*P. vivax*), *Plasmodium malariae* (*P. malariae*) and *Plasmodium ovate* (*P. ovale*) of which *P. falciparum* is responsible for most of the mortality in humans. *P. falciparum* is dangerous not only because it digests the red blood cell's hemoglobin, but also because it changes the adhesive properties of the cell it inhabits, which causes the cell to stick to the walls of blood vessels. This becomes dangerous when the infected blood cells stick to the blood vessels, obstructing blood flow.

The life cycle of the malaria parasite in a human or animal begins when an infected mosquito injects malaria sporozoites into a new host during a blood meal. The sporozoites travel to the liver, where they invade hepatocytes (liver cells) and undergo a replication cycle which leads to the release of thousands of merozoites into the blood stream which happens approximately two weeks later. Released merozoites then invade red blood cells and undergo an intraerythrocytic cycle of development. During the first 48 hours after infecting a red blood cell, a parasite goes through several phases of development. The first phase is the ring stage, in which the parasite begins to metabolize hemoglobin. The next phase is the trophozoite stage, during which the parasite metabolizes most of the hemoglobin, gets larger, and prepares to produce more parasites. Finally, the parasite divides asexually to form a multinucleated schizont. At the end of the cycle, the red blood cell bursts open and the released merozoites invade new red blood cells (see MicroWorlds™ electronic science magazine; Lawrence Berkeley National Laboratory, University of California). As the parasite matures inside the red blood cell, it modifies the adhesive properties of the cell it inhabits which becomes especially dangerous as these infected blood cells stick to the capillaries in the brain, obstructing blood flow, a condition called cerebral malaria. In addition, continuous rupturing of infected and uninfected blood red cells, the latter as a result of an immune-mediated mechanism, coupled to a reduction in the production of new red blood cells from the bone marrow (dyserythropoiesis) inevitably leads to anaemia.

Drug resistant malaria has become one of the most important problems in malaria control. Clinical resistance in vivo has been reported to all antimalarial drugs except artemisinin and its derivatives. The WHO recommendations for the treatment of drug resistant infections include the use of artemisinins in combination with other classes of antimalarials. However, the high cost of these drugs limits their accessibility to poor countries. In some parts of the world, artemisinin drugs constitute the first line of treatment, and are used indiscriminately as monotherapy for self treatment of suspected uncomplicated malaria, which in turn increases the risk of developing drug resistance. The problem of drug resistance can be attributed primarily to increased selection pressures on *P. falciparum* in particular, due to indiscriminate and incomplete drug use for self treatment. Resistance to chloroquine in *P. falciparum*, first reported in Thailand in 1961 is now widespread in most malaria endemic countries. Resistance to the antifolates pyrimethamine and cycloguanil, arose soon after their deployment as antimalarials. The addition of sulfa compounds created drug combinations that in many cases proved effective against the resistant parasites, however, resistance arose due to these combinations as well. Several mechanisms can account for changes in drug susceptibility in the malaria parasites, for example, physiological adaptations due to non genetic changes, selection of previously existing drug resistant parasites from a mixed population under drug pressure, spontaneous mutation, mutation of extranuclear genes, or the existence of plasmid-like factors.

Selection of mutants by the drugs themselves appears to be an important mechanism. In an environment where sub-therapeutic levels of the antimalarial drugs are present, those parasites which have resistance through their natural variation or through mutations clearly have an important biological advantage. This means that even though the resistant strains were initially in the minority, the continued drug mediated elimination of intra-specific competition from the non-resistant strains has allowed the resistant strains to attain numerical superiority, in fact, resistance to conventional antimalarial drugs such as chloroquine and sulfadoxine-pyrimethamine (SP) is widespread. Multidrug resistant *P. falciparum* malaria is highly prevalent in Southeast Asia, South America and Africa. Africa, which is the continent with the highest burden of the disease is also affected with increased mortality as a result (Roll Back Malaria, Facts on ACTs, WHO, January 2006). The majority of studies indicate that drug pressure selection is to blame for the emergence of resistant malaria. In genetically determined resistance, gametocytes from resistant parasite populations will be transmitted, promoting the spread of drug-resistant strains. *Plasmodium* parasites have extremely complex genomes, and the ease with which they can switch between the microenvironments in different hosts, and the metabolic changes required illustrates the difficulty in studying the exact modes of action of the antimalarial drugs on parasite metabolism (The Biology of Malaria Parasites: Report of a WHO Scientific Group. WHO Technical Report Series, 1987). Examples of antimalarials that are associated with drug-resistance are the antibiotic doxycycline, certain antifolates such as proguanil, pyrimethamine and sulfonamides, quinolines such as chloroquine, mefloquine and quinine, and naphthoquinones such as atovaquone.

Certain compounds such as 1,2-dihydrotriazines, 2,4-diaminopyrimidines and 2,4-diaminoquinazolines have been extensively studied as inhibitors of dihydrofolate reductase (DHFR), a key enzyme for maintaining pools of reduced folates. In the malarial parasites, DHFR exists as a part of the bifunctional enzyme dihydrofolate reductase-thymidylate synthase (DHFR-TS), and acts by reducing dihydrofolate to tetrahydrofolate, which is subsequently converted to 5,10-methylenetetrahydrofolate. This cofactor is utilized by thymidylate synthase (TS) to produce deoxythymidylate, a component of DNA which is essential for DNA synthesis and cell growth. Inhibition of DHFR results in inhibition of DNA synthesis and in parasite death. These inhibitors, also known as antifolates, are therefore potentially useful drugs against infectious agents, provided that they can selectively inhibit DHFR of the target parasites without substantially affecting the cells of the host.

Inhibitors of DHFR, generally known as antifolates or antifols, which have been shown to be effective antimalarials, include cycloguanil (Cyc), a 1,2-dihydrotriazine and pyrimethamine (Pyr), a 2,4-diaminopyrimidine, and derivatives thereof, with different substituents on positions 1 and 2 of the dihydrotriazine, and on positions 5 and 6 of the diaminopyrimidine. Some compounds in these classes are also good inhibitors of bacterial DHFR, and have antibacterial activity. Although cycloguanil, pyrimethamine and other described 1,2-dihydrotriazine, 2,4-diaminopyrimidine and 2,4-diaminoquinazoline derivatives are effective against wild type malaria parasites, they are not effective in vivo after oral administration against antifolate-resistant parasites, which have been shown to bear mutations in the DHFR and dihydropteroate synthase (DHPS). The degree of resistance generally increases with the number of DHFR mutations, prompting the need for novel drugs which are effective both against non-resistant and resistant strains of malaria parasites. Since the human host also has DHFR, these drugs must have selectivity for the parasite DHFR over the corresponding host enzyme, or inhibit it to a much lesser degree, as otherwise they may have toxicity to the host. Other characteristics of the drugs must also not lead to host toxicity. It is also preferable that these drugs do not have significant antibacterial activity, since they will have to be administered frequently in malaria endemic areas, to treat malaria re-infections, with the added danger of developing resistant strains of bacteria co-existing during the anti-malarial treatment.

Specific 1,2-dihydrotriazine derivatives such as WR99210 and its prodrug PS-15 are known to be effective inhibitors for some drug-resistant strains of malaria in vitro, although they also show toxicity in animal models (see Knight et al., *Ann. Trop. Med. Parasitol.* (1982) 76:1-7) and their manufacturing involves the production of a highly toxic by-product, TCDD, which must be strictly controlled to a ppb level. Several compounds related to PS-15 have been synthesized and some have been under clinical trials (Jensen et al., *J. Med. Chem.* (2001) 44:3925-31; U.S. Pat. No. 5,322,858 (1994); and Shearer et al., *J. Med. Chem.* (2005) 48:2805-2813). It was speculated that WR99210 binds to the DHFR, but the actual details of binding were unknown until a crystal structure of the enzyme-inhibitor complex was reported revealing molecular interactions between WR99210 and *Plasmodium falciparum* DHFR (Yuvaniyama et al., *Nat. Struct. Biol.* (2003) 10:357-65). Despite their potent in vitro anti-*P. falciparum* activity against non-resistant and antifolate resistant strains, it is unclear whether such compounds will ever be developed as an effective treatment against malaria as a consequence of their poor oral bioavailability.

Because of the increasing mortality associated with malaria, a need exists for better and more effective methods of disease control. In particular, a need exists for more effective treatment and prophylaxis against drug-resistant malaria, i.e., in the form of effective inhibitors of multiple mutant dihydrofolate reductase of *Plasmodium falciparum*. The present invention meets this and other needs.

BRIEF SUMMARY OF THE INVENTION

The present invention relates to antimalarial compounds or antifolates for the treatment and prophylaxis of malaria and methods of making and using the compounds. The antifolates act as novel inhibitors of dihydrofolate reductase (DHFR) of *Plasmodium falciparum* in the treatment of malaria, including non-resistant and drug-resistant malaria.

The present invention provides a compound of Formula I as shown below:

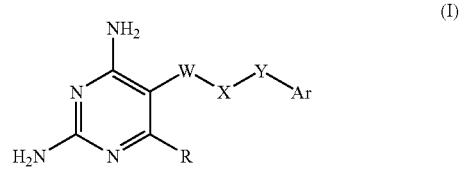

wherein R is hydrogen or $C_{1-4}$ alkyl,
W is O or $CH_2$
X is $(CH_2)_{2-4}$ and is optionally substituted with one or more hydroxyl groups, and
Y is $CH_2$, O, S, or N(Z), wherein Z is H or optionally substituted acyl, alkyl, or aryl or derivative thereof; and
Ar is optionally substituted aryl or heteroaryl or derivative thereof;
or a pharmaceutically acceptable salt thereof.

In one embodiment, Ar is an optionally substituted aromatic ring, such as a substituted phenyl or naphthyl, or an optionally substituted heteroaromatic ring optionally selected from the group of quinolinyl, isoquinolinyl, quinazolinyl, quinoxalinyl, pyridyl, indolyl, triazolyl, benzoxazolyl, benzimidazolyl, indolinyl and benzotriazolyl. When Ar is an aromatic ring, it is optionally substituted by at least one group selected from acyl, benzoxazolyl, nitro, carboxyl, carboxyalkylC(1-3), carboxyalkylC(1-3)oxy, alkylC(1-3)oxycarbonylalkylC(1-3), alkylC(1-3)oxycarbonylalkylC(1-3)oxy, tetrazolyl, tetrazolylalkylC(1-3) and tetrazolylalkylC(1-3)oxy. Ar is optionally substituted by additional substituents. In another embodiment, Ar is substituted at one or more available positions with at least one group selected from alkyl, substituted alkyl, cycloalkyl, substituted cycloalkyl, trifluoromethyl, aryl, substituted aryl, halogen, amino, substituted amino, alkoxy, aryloxy, hydroxyl and nitro.

In one embodiment, R is $C_{1-4}$ alkyl. In another embodiment, R is ethyl.

In one embodiment, W—X—Y is $O(CH_2)_{2-4}O$. In another embodiment, W—X—Y is $O(CH_2)_{2-4}S$. In yet another embodiment W—X—Y is $O(CH_2)_{2-4}NZ$. In a further embodiment W—X—Y is $O(CH_2)_{2-4}$ or $(CH_2)_{3-5}O$.

The present invention further contemplates a method to treat a subject in need of treatment for malaria, which method includes administering to the subject an effective amount of compound I or derivatives thereof. In one embodiment, the subject is in need of treatment for a drug-resistant or non-resistant strain of malaria. In another embodiment, the drug-resistant strain (e.g., antifolate-resistant strain) of malaria is a strain that is resistant to at least one drug (e.g., anti-DHFR drug). Such antifolate drugs include, but are not limited to, cycloguanil, chlorcycloguanil, and pyrimethamine. In one preferred embodiment, the antifolate-resistant strain of malaria has at least one mutation in its DHFR protein sequence, including 16(Ala→Val), 51(Asn→Ile), 59(Cys→Arg), 108(Ser→Asn), 108(Ser→Thr), and 164(Ile→Leu). In another preferred embodiment, the antifolate-resistant strain of malaria is a strain of malaria that has at least two mutations in its DHFR protein sequence, including 16(Ala→Val), 51(Asn→Ile), 59(Cys→Arg), 108(Ser→Asn), 108(Ser→Thr), and 164(Ile→Leu). In another preferred embodiment, the antifolate-resistant strain of malaria is a strain of malaria that has at least two mutations in its DHFR protein sequence, including 16(Ala→Val) and 108 (Ser→Thr). The treatment for uncomplicated malaria including intermittent and/or preventative treatment is preferably via an oral route. The treatment for complicated or severe malaria is preferably via a parenteral route. However, other forms of administration are also contemplated.

BRIEF DESCRIPTION OF THE DRAWINGS

The present invention is best understood when read in conjunction with the accompanying figures, which serve to illustrate the preferred embodiments. It is understood, however, that the invention is not limited to the specific embodiments disclosed in the Figures. The chemical structures shown in the Figures are further discussed in Example 1 of the specification.

Figure 1:
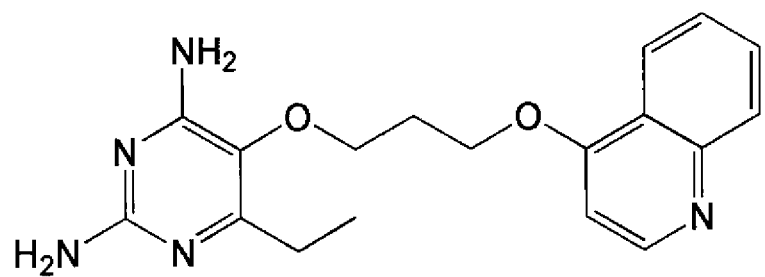
FIG. 1 illustrates the chemical structure of P113.

DETAILED DESCRIPTION OF THE INVENTION i) General Overview

The present invention provides novel inhibitors which are effective against malaria, in particular antifolate-resistant malaria arising from mutations in dihydrofolate reductase (DHFR) of *Plasmodium falciparum* (*P. falciparum*). Known antifolate-resistant *P. falciparum* strains have mutations at positions 108 (serine to asparagine), 51 (asparagine to isoleucine), 59 (cysteine to arginine) and/or 164 (isoleucine to leucine). Another antifolate-resistant strain of *P. falciparum* carries mutations at positions 16 (alanine to valine) and 108 (serine to threonine). It is possible that they act not only on dihydrofolate reductase, but also on other targets in the malarial parasites or host responses leading to effective parasite killing. The antimalarial compounds of the present invention have relatively low toxicity to the mammalian host and are potent when administered in pharmaceutical compositions. One major advantage of the invention is that the novel compounds show little or no antibacterial activity and are, thus, highly unlikely to lead to resistant strains of bacteria.

ii) Definitions

The terms "antifolates", "antifols" and "DHFR inhibitors" are interchangeably used herein and, for the purpose of this invention, refer to compounds that can be used in the treatment or prophylaxis of malaria. These compounds are effective inhibitors of the mutant and wild-type dihydrofolate reductase (DHFR) of *Plasmodium falciparum* (*P. falciparum*).

The terms "*Plasmodium falciparum*" and "*P. falciparum*" are interchangeably used herein and refer to the parasite that is transmitted to human and animal hosts, resulting in the host showing one or more symptoms of malaria. More specifically, *P. falciparum* is a protozoan that causes malaria.

The term "acyl" as used herein refers to a group of the form R"C(=O)—, wherein R" is for example H, $C_{1-6}$ alkyl, aryl, $C_{1-6}$ alkoxy, OH, $NH_2$, NHR", or $N(R')_2$, wherein R' is $C_{1-6}$ alkyl or aryl.

As used herein, the terms "alkyl," "alkenyl" and "alkynyl" include straight-chain, branched-chain and cyclic monovalent hydrocarbyl radicals, and combinations of these, which contain only C and H when they are unsubstituted. Examples include methyl, ethyl, isobutyl, cyclohexyl, cyclopentylethyl, 2-propenyl, 3-butynyl, and the like. The total number of carbon atoms in each such group is sometimes described herein, e.g., when the group can contain up to ten carbon atoms it can be represented as 1-10C or as C1-C10 or C1-10. When heteroatoms (N, O and S typically) are allowed to replace carbon atoms as in heteroalkyl groups, for example, the numbers describing the group, though still written as e.g. C1-C6, represent the sum of the number of carbon atoms in the group plus the number of such heteroatoms that are included as replacements for carbon atoms in the ring or chain being described.

Typically, the alkyl, alkenyl and alkynyl substituents of the invention contain 1-10C (alkyl) or 2-10C (alkenyl or alkynyl). Preferably they contain 1-8C (alkyl) or 2-8C (alkenyl or alkynyl). Sometimes they contain 1-4C (alkyl) or 2-4C (alkenyl or alkynyl). A single group can include more than one type of multiple bond, or more than one multiple bond; such groups are included within the definition of the term "alkenyl" when they contain at least one carbon-carbon double bond, and are included within the term "alkynyl" when they contain at least one carbon-carbon triple bond.

Alkyl, alkenyl and alkynyl groups are often substituted to the extent that such substitution makes sense chemically. Typical substituents include, but are not limited to, halo, =O, =N—CN, =N—OR, =NR, OR, $NR_2$, SR, $SO_2R$, $SO_2NR_2$, $NRSO_2R$, $NRCONR_2$, NRCOOR, NRCOR, CN, COOR, $CONR_2$, OOCR, COR, and $NO_2$, wherein each R is independently H, C1-C8 alkyl, C2-C8 heteroalkyl, C1-C8 acyl, C2-C8 heteroacyl, C2-C8 alkenyl, C2-C8 heteroalkenyl, C2-C8 alkynyl, C2-C8 heteroalkynyl, C6-C10 aryl, or C5-C10 heteroaryl, and each R is optionally substituted with halo, =O, =N—CN, =N—OR', =NR', OR', $NR'_2$, SR', $SO_2R'$, $SO_2NR'_2$, NR'$SO_2$R', NR'CONR'$_2$, NR'COOR', NR'COR', CN, COOR', CONR'$_2$, OOCR', COR', and $NO_2$, wherein each R' is independently H, C1-C8 alkyl, C2-C8 heteroalkyl, C1-C8 acyl, C2-C8 heteroacyl, C6-C10 aryl or C5-C10 heteroaryl. Alkyl, alkenyl and alkynyl groups can also be substituted by C1-C8 acyl, C2-C8 heteroacyl, C6-C10 aryl or C5-C10 heteroaryl, each of which can be substituted by the substituents that are appropriate for the particular group.

While "alkyl" as used herein includes cycloalkyl and cycloalkylalkyl groups, the term "cycloalkyl" may be used herein to describe a carbocyclic non-aromatic group that is connected via a ring carbon atom, and "cycloalkylalkyl" may be used to describe a carbocyclic non-aromatic group that is connected to the molecule through an alkyl linker. Similarly, "heterocyclyl" may be used to describe a non-aromatic cyclic group that contains at least one heteroatom as a ring member and that is connected to the molecule via a ring atom, which may be C or N; and "heterocyclylalkyl" may be used to describe such a group that is connected to another molecule through a linker. The sizes and substituents that are suitable for the cycloalkyl, cycloalkylalkyl, heterocyclyl, and heterocyclylalkyl groups are the same as those described above for alkyl groups. As used herein, these terms also include rings that contain a double bond or two, as long as the ring is not aromatic.

"Aromatic" moiety or "aryl" moiety refers to a monocyclic or fused bicyclic moiety having the well-known characteristics of aromaticity; examples include phenyl and naphthyl. Similarly, "heteroaromatic" and "heteroaryl" refer to such monocyclic or fused bicyclic ring systems which contain as ring members one or more heteroatoms selected from O, S and N. The inclusion of a heteroatom permits aromaticity in 5-membered rings as well as 6-membered rings. Typical heteroaromatic systems include monocyclic C5-C6 aromatic groups such as pyridyl, pyrimidyl, pyrazinyl, thienyl, furanyl, pyrrolyl, pyrazolyl, thiazolyl, oxazolyl, and imidazolyl, and the fused bicyclic moieties formed by fusing one of these monocyclic groups with a phenyl ring or with any of the heteroaromatic monocyclic groups to form a C8-C10 bicyclic group such as indolyl, benzimidazolyl, indazolyl, benzotriazolyl, isoquinolyl, quinolyl, benzothiazolyl, benzofuranyl, pyrazolopyridyl, quinazolinyl, quinoxalinyl, cinnolinyl, and the like. Any monocyclic or fused ring bicyclic system which has the characteristics of aromaticity in terms of electron distribution throughout the ring system is included in this definition. It also includes bicyclic groups where at least the ring which is directly attached to the remainder of the molecule has the characteristics of aromaticity. Typically, the ring systems contain 5-12 ring member atoms. Preferably the monocyclic heteroaryls contain 5-6 ring members, and the bicyclic heteroaryls contain 8-10 ring members.

Aryl and heteroaryl moieties may be substituted with a variety of substituents including C1-C8 alkyl, C2-C8 alkenyl, C2-C8 alkynyl, C5-C12 aryl, C1-C8 acyl, and heteroforms of these, each of which can itself be further substituted; other substituents for aryl and heteroaryl moieties include halo, OR, $NR_2$, SR, $SO_2R$, $SO_2NR_2$, $NRSO_2R$, $NRCONR_2$, NRCOOR, NRCOR, CN, COOR, $CONR_2$, OOCR, COR, and $NO_2$, wherein each R is independently H, C1-C8 alkyl, C2-C8 heteroalkyl, C2-C8 alkenyl, C2-C8 heteroalkenyl, C2-C8 alkynyl, C2-C8 heteroalkynyl, C6-C10 aryl, C5-C10 heteroaryl, C7-C12 arylalkyl, or C6-C12 heteroarylalkyl, and each R is optionally substituted as described above for alkyl groups. The substituent groups on an aryl or heteroaryl group may of course be further substituted with the groups described herein as suitable for each type of such substituents or for each component of the substituent. Thus, for example, an arylalkyl substituent may be substituted on the aryl portion with substituents described herein as typical for aryl groups, and it may be further substituted on the alkyl portion with substituents described herein as typical or suitable for alkyl groups.

"Optionally substituted" as used herein indicates that the particular group or groups being described may have no non-hydrogen substituents, or the group or groups may have one or more non-hydrogen substituents. If not otherwise specified, the total number of such substituents that may be present is equal to the number of H atoms present on the unsubstituted form of the group being described. Where an optional substituent is attached via a double bond, such as a carbonyl oxygen (=O), the group takes up two available valences, so the total number of substituents that may be included is reduced according to the number of available valences.

The term "strain" refers to a specific genetic variant of a particular organism. In chemotherapy, microorganisms can be described as being drug resistant or non-resistant strains according to their susceptibility to a particular drug or therapy. Often, a drug-resistant strain will have one or more genetic mutations. A non-resistant strain is a strain that is normally fully responsive to a particular drug or therapy. Such a strain may or may not have genetic mutations. A resistant strain is a strain that is less responsive than a non-resistant strain to the same drug or therapy.

The terms "non-resistant" and "wild type" are interchangeably used herein and refer to strains of the parasite that are normally fully responsive to a particular drug or therapy.

iii) The Antimalarial Compounds

In one aspect, the invention provides a series of novel antimalarial compounds which are effective against both, wild type- and drug-resistant-, including antifolate-resistant malaria caused by *Plasmodium falciparum* (*P. falciparum*). These compounds belong to the class of dihydrofolate reductase inhibitors. The novel compounds are based on Formula I as shown below:

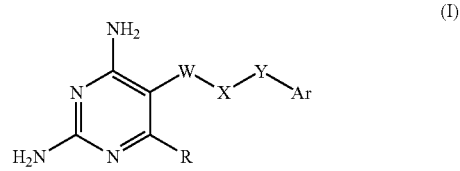

(I)

R in compounds of Formula (I) is H or $C_1$-$C_4$ alkyl, and in some embodiments it is $C_{1-4}$ alkyl. In certain embodiments, R is ethyl or methyl; ethyl is sometimes preferred.

W is sometimes O and sometimes it is $CH_2$. In some preferred embodiments, W is O.

Y is often $CH_2$, O, S or NZ.

X is a two to four carbon alkylene chain, $(CH_2)_{2-4}$, that may be substituted with a hydroxyl group.

Ar is sometimes preferably a heterocyclic aromatic group such as quinolinyl, isoquinolinyl, quinazolinyl, or quinoxalinyl. In some preferred embodiments, Ar is quinolinyl and in particular embodiments it is 4-quinolinyl.

When Ar is an aromatic ring rather than a heteroaromatic group, it must be substituted by at least one group, and in some embodiments it is substituted by at least one group selected from the group consisting of acyl, benzoxazolyl, nitro, carboxyl, carboxyalkylC(1-3), carboxyalkylC(1-3)oxy, alkylC(1-3)oxycarbonylalkylC(1-3), alkylC(1-3)oxycarbonylalkylC(1-3)oxy, tetrazolyl, tetrazolylalkylC(1-3) and tetrazolylalkylC(1-3)oxy; and Ar is optionally substituted by additional substituents or a pharmaceutically acceptable salt thereof. In some embodiments, Ar is substituted by at least one group selected from the group consisting of $CO_2R'$, $(CH_2)_{1-3}COOR'$, $O(CH_2)_{1-3}COOR'$, tetrazolyl, $(CH_2)_{1-3}$-tetrazolyl, and $O(CH_2)_{1-3}$-tetrazolyl, wherein R' is H or $C_{1-4}$ alkyl. In another embodiment, Ar may be further substituted at one or more available positions by an optional substituent selected from alkyl, substituted alkyl, cycloalkyl, substituted cycloalkyl, trifluoromethyl, aryl, substituted aryl, halogen, amino, substituted amino, alkoxy, aryloxy, hydroxyl, nitro and the like. Preferred optional substituents for Ar include halo, $CF_3$, methoxy, and methyl, and Ar typically contains 0-2 and preferably 0 or 1 such optional substituents.

When Ar is heteroaromatic ring, it may be substituted at one or more available positions by an alkyl, substituted alkyl, cycloalkyl, substituted cycloalkyl, trifluoromethyl, aryl, substituted aryl, halogen, amino, substituted amino, alkoxy, aryloxy, hydroxyl, nitro and the like. Preferred substituents for Ar when it is a heteroaromatic ring include halo, $CF_3$, methoxy, and methyl, and in some embodiments the heteroaromatic group represented by Ar is unsubstituted.

The antimalarial compounds of the presented invention include their tautomers and pharmaceutically acceptable salts. The invention also includes pharmaceutical compositions containing at least one compound of Formula (I) admixed with at least one pharmaceutically acceptable excipient. In preferred embodiments, the excipient is not water. Where a chiral center is present in a compound of Formula (I), the invention includes each individual enantiomer or diastereomer of the compound as well as mixtures of enantiomers or diastereomers, including racemic mixtures.

The invention also includes prodrugs that are readily transformed in vivo into a compound of Formula (I). Examples of these prodrugs include substituted derivatives wherein an amine nitrogen is substituted with an acyl group, typically a C1-C6 acyl group that may be substituted, and compounds wherein a carboxyl group is esterified into a C1-C6 alkoxycarbonyl group. Prodrugs substituted with an N acyl that is a C1-C4 acyl group or an acyl group derived from an amino acid such as glycine, alanine, serine, glutamine, valine, leucine, isoleucine, glutamate, aspartate, and the like, or dipeptides or tripeptides of these amino acids, are often preferred because they are readily deacylated by endogenous amidases and esterases.

Further encompassed are the synthetic processes of making the above compounds. The synthetic processes of making 5-alkoxy-6-substituted-2,4-diaminopyrimidines in certain embodiments involve O-alkylation of 5-hydroxy-6-substituted-2,4-diaminopyrimidine with alkyl halide or alkyl mesylate in the presence of a base.

In another aspect, the invention provides methods of using the compounds for the treatment of malaria, including non-resistant and drug-resistant strains of malaria. In a preferred embodiment, the disclosed compounds are effective inhibitors against both wild-type and resistant *Plasmodium falciparum* dihydrofolate reductase (pf DHFR). Further contemplated is the use of the disclosed compounds, or a pharmaceutical composition or salt thereof, in the treatment of resistant malaria derived from *Plasmodium falciparum* carrying wild-type or mutant dihydrofolate reductase (pf DHFR), such as the mutant strains described herein having at least one mutation in the DHFR protein sequence, or other strains containing at least one of the point mutations described herein, and more preferably mutant strains containing at least two of the mutations described herein.

iv) Synthesis of the Antimalarial Compounds

The flexible side-chain part of the compounds wherein Ar is a heteroaromatic group is preferably constructed by an alkylation reaction of Ar or ArOH with an alkylating agent as illustrated in Scheme 1 below.

Scheme 1

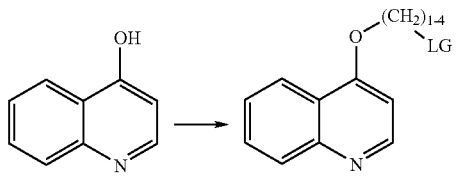

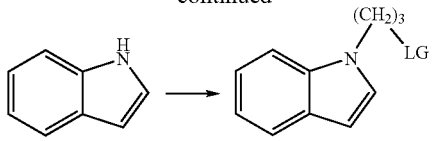

Suitable alkylating agents that produce an alkylated compound useful in synthesis of compounds of Formula (I) are well known. For example, 1,3-dibromopropane or 1-bromo-3-chloropropane can be used in the reactions illustrated above to make compounds having the Formula Ar—(CH$_2$)$_3$—Br or Ar—O—(CH$_2$)$_3$—Br. These intermediates are readily used to alkylate a 5-hydroxy group on a 2,4-diaminopyrimidine to provide compounds of Formula (I). Suitable leaving groups (LG) include, but are not limited to, chemicals such as chloride, bromide, iodide, mesylate, benzenesulfonate, tosylate, and triflate. The variations of this type of reaction would be readily apparent to those of skill in the art. Suitable nucleophiles include, but are not limited to, phenols, other aryl and heteroaryl alcohols, aryl and heteroaryl thiols, thiophenol, aryl and heteroaryl amines, and heteroaromatic compounds that are readily alkylated on a ring atom such as indoles, triazoles, imidazoles, and their substituted derivatives and conjugated bases.

When selective monoalkylation is more difficult to achieve, it is also possible to start from a ω-halogenated alcohol such as 2-bromoethanol, 3-bromopropanol or 3-chloropropanol in place of the bis-electrophile. In that case the OH group in the intermediate alcohol should be changed to a more reactive leaving group provided that it is compatible with the structures of the other parts of the molecule. For example, bromination can be affected by PBr$_3$, aq HBr, Ph$_3$PBr$_2$, CBr$_4$/Ph$_3$P, NBS/Ph$_3$P while mesylation can be affected by MsCl/Et$_3$N. Alternatively, a Mitsunobu reaction (DEAD/Ph$_3$P or DIAD/Ph$_3$P) between the halogenated alcohol and the nucleophile (ArYH) allows for a direct synthesis of the necessary intermediate having a reactive side chain linked to Ar.

Once the reactive side chain containing Ar is synthesized, a further alkylation reaction of the Ar—(CH$_2$)$_{1-4}$-LG species with 5-hydroxy-6-substituted-2,4-diaminopyrimidines in the presence of a base yields the compounds of the present invention. 5-Hydroxy-6-substituted-2,4-diaminopyrimidines are readily available from commercial sources. The base can be selected from LiH, LiOH, KOH, NaH and K$_2$CO$_3$, wherein the most preferred base is LiOH. The base can be added at 1-10 equivalents relative to the hydroxypyrimidines. The reaction is preferably carried out in an inert solvent, wherein N,N-dimethylformamide is the preferred solvent. The reaction can be carried out between about 25-80° C. but preferably at 25-30° C. For a more detailed description of the reaction see the following patents and publications incorporated herein by reference in their entirety (i.e., U.S. Pat. Nos. 4,179,562 and 4,374,136; GB 2086386). Other methods for making compounds of this general structure are well known in the art, and are readily adapted for preparation of these compounds by the skilled practitioner.

The final products can be isolated and purified by conventional techniques such as evaporation, extraction, crystallization and/or column chromatography. Hydrochloride and other pharmaceutically acceptable salts of the compounds of Formula (I) are readily prepared by admixing the compound with an appropriate acid corresponding to the desired salt, as is well known in the art. The acid is often added to a solution or suspension of the compound of Formula (I) in a solvent comprising water, methanol and/or ethanol, followed by evaporation to remove any undesired solvent. The diaminopyrimidines are often converted to a di-salt such as a dihydrochloride salt.

v) Pharmaceutical Compositions and Formulations of the Antimalarial Compounds The antimalarial compounds or antifolates may be formulated as pharmaceuticals to be used in the methods of the invention. A composition or compound that can stimulate a biological response associated with the binding of the antimalarial compound to wild type and mutant (e.g., single mutant, multiple mutant) dihydrofolate reductase (DHFR) of *P. falciparum* in drug resistant and non-resistant malaria can be used as a pharmaceutical in the invention. Examples of such general details on techniques for formulation and administration are well described in the scientific literature (see *Remington's Pharmaceutical Sciences*, Maack Publishing Co., Easton Pa.). Antifolate pharmaceutical formulations can be prepared according to any method known in the art for the manufacture of pharmaceuticals. The antifolates used in the methods of the invention can be formulated for administration in any conventionally acceptable way including via oral administration and via parenteral routes. Oral administration is preferred for treatment of uncomplicated malaria while parenteral administration is preferred for treatment of complicated (severe) malaria. Illustrative examples are set forth below.

TABLE 1

Anti-malarial activity and oral bioavailability of triazines compared to pyrimidine.

| | $IC_{50}$ against *P. falciparum* in vitro (µM) | | $ED_{90}$ *P. chabaudi* AS | | |
|---|---|---|---|---|---|
| | Wild Type | Resistant mutant | s.c. (mg/kg) | oral | Oral BA in rats (%) |
| WR99210 | 0.0006 | 0.018 | 1.1 | 74.2 | <1 |
| Cycloguanil | 0.037 | >100 | 3.7 | 6.2 | 59.3 |
| Pyrimethamine | 0.079 | >100 | 0.25 | 0.88 | ~100 |

Table 1 above shows the anti-malarial activity and oral bioavailability of conventional dihydrotriazines compared to conventional pyrimidine. Although WR99210 is active against non-resistant and pyrimethamine resistant strains of *P. falciparum* parasites in vitro and in vivo after subcutaneous administration to mice infected with *P. chabaudi* AS, its efficacy is substantially reduced if the compound is administered by the oral route (i.e., high $ED_{90}$ value). This reduction has been found to be due to the poor oral bioavailability of WR99210 compared to cycloguanil and pyrimethamine.

TABLE 2

Antibacterial activities of the novel 2,4-diaminopyrimidine derivative compounds compared to trimethoprim and pyrimethamine.

| | Minimal inhibitory concentration (µM) | |
|---|---|---|
| Compounds | *S. aureus* | *E. coli* |
| Trimethoprim | 1 < MIC < 10 | 1 < MIC < 10 |
| Pyrimethamine | >50 | >50 |
| P135 | >50 | >50 |

TABLE 2-continued

Antibacterial activities of the novel 2,4-diaminopyrimidine derivative compounds compared to trimethoprim and pyrimethamine.

| | Minimal inhibitory concentration (µM) | |
|---|---|---|
| Compounds | *S. aureus* | *E. coli* |
| P149 | 1 < MIC < 10 | 10 < MIC < 50 |
| P153 | 10 < MIC < 50 | 10 < MIC < 50 |
| P154 | >50 | 10 < MIC < 50 |
| P157 | >25 | >25 |
| P171 | >50 | >50 |

In comparison, Table 2 above shows the anti-bacterial activities of the new 2,4-diaminopyrimidine derivative compounds of the present invention. These selected compounds are inactive against *S. aureus* and *E. coli* and require very high micromolar concentrations to completely inhibit bacterial growth on agar plates, whereas other 2,4-diaminopyrimidine derivatives such as trimethoprim are clinically efficacious antibiotics.

Pharmaceutical formulations and preparations for oral administration can be prepared using pharmaceutically acceptable carriers well known in the art in dosages suitable for oral administration. Such carriers enable the pharmaceutical formulations to be formulated in unit dosage forms as tablets, pills, powder, capsules, liquids, lozenges, gels, syrups, slurries, suspensions, and the like, suitable for ingestion by the patient. Pharmaceutical preparations for oral use can be prepared by combining antifolate compounds with a solid excipient, optionally grinding a resulting mixture, and processing the mixture of granules, after adding suitable additional compounds, if desired, to obtain tablets or pills. Suitable solid excipients are carbohydrate or protein fillers which include, but are not limited to, sugars, including lactose, sucrose, mannitol, or sorbitol; starch from corn, wheat, rice, potato, or other plants; cellulose such as methyl cellulose, hydroxypropylmethyl-cellulose, or sodium carboxymethyl-cellulose; and gums including arabic and tragacanth; as well as proteins such as gelatin and collagen. If desired, disintegrating or solubilizing agents may be added, such as the cross-linked polyvinyl pyrrolidone, agar, alginic acid, or a salt thereof, such as sodium alginate.

Pharmaceutical preparations of the invention that can also be used orally are, for example, push-fit capsules made of gelatin, as well as soft, sealed capsules made of gelatin and a coating such as glycerol or sorbitol. Push-fit capsules can contain antifolate mixed with a filler or binders such as lactose or starches, lubricants such as talc or magnesium stearate, and, optionally, stabilizers. In soft capsules, the antifolate compounds may be dissolved or suspended in suitable liquids, such as fatty oils, liquid paraffin, or liquid polyethylene glycol with or without stabilizers.

Aqueous suspensions of the invention contain an antifolate in admixture with excipients suitable for the manufacture of aqueous suspensions. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan monooleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Oil suspensions can be formulated by suspending an antifolate in a vegetable oil, such as arachis oil, olive oil, sesame oil or coconut oil, or in a mineral oil such as liquid paraffin. The oil suspensions can contain a thickening agent, such as beeswax, hard paraffin or cetyl alcohol. Sweetening agents can be added to provide a palatable oral preparation. These formulations can be preserved by the addition of an antioxidant such as ascorbic acid.

Dispersible powders and granules of the invention suitable for preparation of an aqueous suspension by the addition of water can be formulated from an antifolate in admixture with a dispersing, suspending and/or wetting agent, and one or more preservatives. Suitable dispersing or wetting agents and suspending agents are exemplified by those disclosed above. Additional excipients, for example sweetening, flavoring and coloring agents, can also be present.

The pharmaceutical formulations of the invention can also be in the form of oil-in-water emulsions. The oily phase can be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening and flavoring agents. Syrups and elixirs can be formulated with sweetening agents, such as glycerol, sorbitol or sucrose. Such formulations can also contain a demulcent, a preservative, a flavoring or a coloring agent.

When the drugs are delivered by intravenous or other parenteral routes via injection, the antifolate pharmaceutical formulations of the invention can be in the form of a sterile injectable preparation, such as a sterile injectable aqueous solution. The sterile injectable preparation can also be a sterile injectable solution in a nontoxic parenterally-acceptable diluent or solvent. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables.

EXAMPLES

The examples below are provided to illustrate the invention but not to limit its scope. Other variants of the invention will be readily apparent to one of ordinary skill in the art and are encompassed by the appended claims. All publications, patents, and patent applications cited herein are hereby incorporated by reference in their entirety.

Example 1

2,4-diamino-6-ethyl-5-(3-(quinolin-4-yloxy)propoxy)pyrimidine (P113) (See FIG. 1)

A representative procedure for the preparation of 2,4-diamino-6-ethyl-5-(3-(quinolin-4-yloxy)propoxy)pyrimidine dihydrochloride is provided below:

a) 3-(quinolin-4-yloxy)propan-1-ol

A suspension of quinolin-4-ol (1.35 g, 9.30 mmol), anhydrous potassium carbonate (3.73 g, 26 mmol) and potassium iodide (4.23 g) in anhydrous DMF (8 mL) was stirred at 25° C. for 30 minutes. 3-Chloropropanol (2.93 g, 31 mmol) was added and the reaction was stirred until the starting material was consumed. The reaction was diluted with dichloromethane and extracted with water. The product was obtained as a slightly yellow solid (0.5298 g, 28%) after evaporation of the dichloromethane layer, and was used for the next step without further purification. $^1$H NMR (400 MHz, CDCl$_3$): 2.09 (2H, m), 3.93 (2H, t, J=5.6 Hz), 4.10 (2H, t, J=5.6 Hz), 4.51 (11H, s), 6.25 (1H, d, J=5.5 Hz), 7.32 (1H, t, J=7.4 Hz), 7.56 (1H, t, J=8.2 Hz), 7.90 (1H, d, J=8.4 Hz), 7.93 (1H, d, J=8.4 Hz), 8.36 (1H, d, J=5.3 Hz).

b) 3-(quinolin-4-yloxy)propyl mesylate

A solution of the 3-(quinolin-4-yloxy)propan-1-ol obtained in step a) (0.5298 g, 2.6 mmol) was treated with triethylamine (0.60 mL) and methanesulfonyl chloride (0.55 g, 4.8 mmol) in dichloromethane (5 mL). After the starting material was consumed, the reaction was diluted with dichloromethane, washed with water, aq NaHCO$_3$ and evaporated. The residue was purified by column chromatography on SiO$_2$ and eluted with ethyl acetate. The product was obtained as a light yellow solid (0.3868 g, 53%). $^1$H NMR (400 MHz, CDCl$_3$): 2.43 (2H, m), 3.00 (3H, s), 4.38 (2H, t, J=5.8 Hz), 4.55 (2H, t, J=5.8 Hz), 6.80 (1H, d, J=5.5 Hz), 7.55 (1H, t, J=8.0 Hz), 7.75 (1H, ddd, J=1.2, 7.0, 8.2 Hz), 8.20 (1H, d, J=8.4 Hz), 8.13 (1H, d, J=8.4 Hz), 8.77 (1H, d, J=5.3 Hz).

c) 2,4-diamino-6-ethyl-5-(3-(quinolin-4-yloxy)propoxy)pyrimidine 2,4-diamino-6-ethyl-5-hydroxypyrimidine (0.3963 g, 2.6 mmol) was added to a stirred solution of lithium hydroxide monohydrate (497.2 mg, 11.8 mmol) in DMF (2 mL) and the reaction mixture was stirred for 1 hour. A solution of 3-(quinolin-4-yloxy)-propyl mesylate (0.3868 g, 1.37 mmol) in DMF (1 mL) was slowly added and the reaction mixture was left stirring at 25° C. overnight. The reaction was diluted with dichloromethane and extracted with water. The dichloromethane layer was evaporated followed by crystallization of the residue from aqueous methanol. The product was obtained as a slightly yellow solid (0.4677 g, 53%). $^1$H NMR (400 MHz, DMSO-d$_6$): 0.87 (3H, t, J=7.0 Hz), 2.24 (2H, q, J=7.0 Hz), 2.30 (2H, m), 3.85 (2H, t, J=5.5 Hz), 4.43 (2H, t, J=5.5 Hz), 5.53 (2H, s), 6.11 (2H, s), 7.06 (1H, d, J=5.2 Hz), 7.54 (1H, t, J=8.0 Hz), 7.72 (1H, ddd, J=1.4, 6.9, 8.3 Hz), 7.93 (1H, d, J=8.3 Hz), 8.15 (1H, d, J=8.5 Hz), 8.72 (1H, d, J=5.2 Hz).

d) 2,4-diamino-6-ethyl-5-(3-(quinolin-4-yloxy)propoxy)pyrimidine dihydrochloride 2,4-diamino-6-ethyl-5-(3-(quinolin-4-yloxy)propoxy)pyrimidine (0.1740 g, 0.51 mmol) was suspended in methanol (1 mL) and 2 equivalents of concentrated HCl was added. The titled compound was obtained, after evaporation and trituration of the residue with acetonitrile, as an off-white crystalline solid (0.2004 g, 95%). $^1$H NMR (400 MHz, DMSO-d$_6$): 1.04 (3H, t, J=7.6 Hz), 2.42 (2H, m), 2.45 (2H, t, J=7.0 Hz), 3.97 (2H, t, J=5.9 Hz), 4.72 (2H, t, J=5.9 Hz), 7.56 (2H, bs), 7.61 (1H, d, J=6.7 Hz), 7.87 (1H, t, J=7.8 Hz), 7.97 (1H, s), 8.11 (1H, ddd, J=1.0, 7.3, 8.2 Hz), 8.35-8.40 (3H, m), 9.18 (1H, d, J=6.6 Hz), 12.86 (1H, s).

Other compounds displaying in vitro and in vivo antibacterial activities including free bases and hydrochloride salts are shown below and were prepared by a procedure like the one shown in Example 1 here for P113. Such compounds begin with the appropriate 4-quinolinol starting materials, which are known in the art, and are converted into compounds of Formula (I) by adaptations of these methods that would be readily apparent to those skilled in the art. Exemplary compounds are shown below.

Example 2

Figure 2:
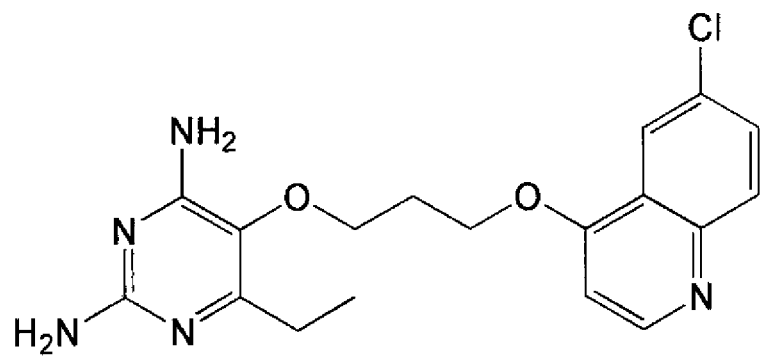
FIG. 2 illustrates the chemical structure of P149.

2,4-diamino-6-ethyl-5-(3-(6-chloro-quinolin-4-yloxy)propoxy)pyrimidine (P149) (See FIG. 2)

a) 6-Chloroquinolin-4-ol

A mixture of 2,2-dimethyl-1,3-dioxane-4,6-dione (Meldrum's acid, 21.62 g, 0.15 mol) and trimethyl orthoformate (150 mL) was heated to a gentle reflux under nitrogen for 1 hour. The resulting red solution was cooled (80° C.) and 4-chloroaniline (19.14 g, 0.15 mol) was added portionwise resulting in the formation of a yellow solid. The reaction mixture was heated to reflux, stirred vigorously for an additional hour, and then cooled to 25° C. (see Ryan et al. (2006) *Org. Lett.* 8:2779-2782; Madrid et al. (2005) *Bioorg. Med. Chem. Lett.* 15:1015-1018). The resulting solid was filtered and washed with cold acetone to afford the ene-amine compound (29.58 g, 70%, mp. 214-214.5° C. (dec.)) as yellow solid which was characterized by $^1$H NMR. To a solution diphenyl ether (20 mL) at 240° C. was added the ene-amine compound (5 g, 17.75 mmol) in small portions resulting in vigorous gas evolution and the reaction was bought to reflux for 30 minutes under nitrogen. The reaction mixture was allowed to cool to 80° C. and the precipitate was isolated by filtration and washing with acetone and hexane until the filtrate was colorless. The brown solid was purified by digestion with ether followed by distillation under reduced pressure to give 6-chloroquinolin-4-ol as light-yellow solid in 55% yield (1.7533 g, m.p. 281-282.5° C. (see Riegel et al., (1946) *J. Am. Chem. Soc.* 68:1264-1266, m.p. 274-275° C.). $^1$H NMR (400 MHz, CDCl$_3$): 6.07 (1H, d, J=7.4 Hz), 7.59 (1H, d, J=8.8 Hz), 7.68 (1H, dd, J=8.8, 2.5 Hz), 7.95 (1H, d, J=7.4 Hz), 8.01 (1H, d, J=2.4 Hz), 11.92 (1H, bs).

b) 3-(6-chloroquinolin-4-yloxy)propyl bromide

To a suspension solution of 6-chloroquinolin-4-ol (2.16 g, 12 mmol), triphenylphosphine (3.78 g, 14.4 mmol, 1.2 eq.), and 3-bromo-1-propanol (1.30 ml, 14.4 mmol, 1.2 eq.) in dry tetrahydrofuran (40 mL) was added diethyl azodicarboxylate (2.51 g, 14.4 mmol, 1.2 eq.) at 25° C. over 20 minutes under nitrogen and the reaction mixture was left stirring for an additional hour. Hydrobromic acid (1.36 mL, 12 mmol, 48% aqueous solution, 1.0 eq.) was added resulting in white solid as the corresponding hydrobromide salt. The white salt was filtered and digested with three times of diethyl ether. The white salt was neutralized by aqueous potassium carbonate solution and followed by extraction with dichloromethane. Upon evaporation of the dichloromethane layers gave the crude product which was subjected to purify by column chromatography (silica gel, 2% methanol in CH$_2$Cl$_2$ as eluent) to provide the bromo compound as white solid (2.52 g, 70%, m.p. 102-103.5° C. (dec.)). $^1$H NMR (500 MHz, CDCl$_3$): 2.50 (2H, m), 3.70 (2H, t, J=6.3 Hz), 4.36 (2H, t, J=5.8 Hz), 6.79 (1H, d, J=5.3 Hz), 7.64 (1H, dd, J=9.0, 2.4 Hz), 7.99 (1H, d, J=9.0 Hz), 8.14 (1H, d, J=2.4 Hz), 8.75 (1H, d, J=5.2 Hz).

c) 2,4-diamino-6-ethyl-5-(3-(6-chloroquinolin-4-yloxy)propoxy)pyrimidine 2,4-Diamino-6-ethyl-5-hydroxypyrimidine (1.39 g, 9 mmol) was added to a stirred solution of lithium hydroxide monohydrate (1.32 g, 31.50 mmol) in DMF (5 mL) and the reaction mixture was stirred at 25° C. for 1 hour. A solution of 3-(6-chloroquinolin-4-yloxy)propyl bromide (2.71 g, 9 mmol) in DMF (3 mL) was added and the reaction mixture was left stirring at 25° C. overnight. DMF was partially removed under reduced pressure to give residue. The residue was digested with dichloromethane and filtered to give white solid. Recrystallization with aqueous methanol and hot water afforded the desired diaminopyrimidine as white solid (1.85 g, 55%, m.p. 230-231° C. (dec.)). $^1$H NMR (500 MHz, DMSO-d$_6$): 0.91 (3H, t, J=7.6 Hz), 2.26 (2H, q, J=7.6 Hz), 2.31 (2H, m), 3.86 (2H, t, J=6 Hz), 4.45 (2H, t, J=5.9 Hz), 5.59 (2H, s), 6.17, (2H, s), 7.15 (1H, d, J=5.3 Hz), 7.76 (1H, dd, J=9.0, 2.4 Hz), 7.98 (1H, d, J=9.0 Hz), 8.14 (1H, d, J=2.4 Hz), 8.77 (1H, d, J=5.2 Hz).

d) 2,4-diamino-6-ethyl-5-(3-(6-chloroquinolin-4-yloxy)propoxy)pyrimidine dihydrochloride To a suspension of 2,4-diamino-6-ethyl-5-(3-(6-chloro-quinolin-4-yloxy)propoxy)pyrimidine (0.5608 g, 1.5 mmol) in methanol (1 mL) was added two equivalents of concentrated HCl. The titled compound was obtained, after trituration of the reaction mixture with diethyl ether, as a off-white crystalline solid (0.6366 g, 95%). $^1$H NMR (500 MHz, DMSO-d$_6$): 1.09 (3H, t, J=7.7 Hz), 2.43 (2H, m), 2.48 (2H, m), 3.99 (2H, t, J=6.2 Hz), 4.70 (2H, t, J=5.9 Hz), 7.55 (2H, bs), 7.64 (1H, d, J=6.6 Hz), 7.95 (1H, s), 3.15 (1H, dd, J=9.1, 2.4 Hz), 8.37 (2H, m), 8.41 (1H, d, J=9.1 Hz), 9.22 (1H, d, J=6.5 Hz), 12.80 (1H, s).

Example 3

Figure 3:
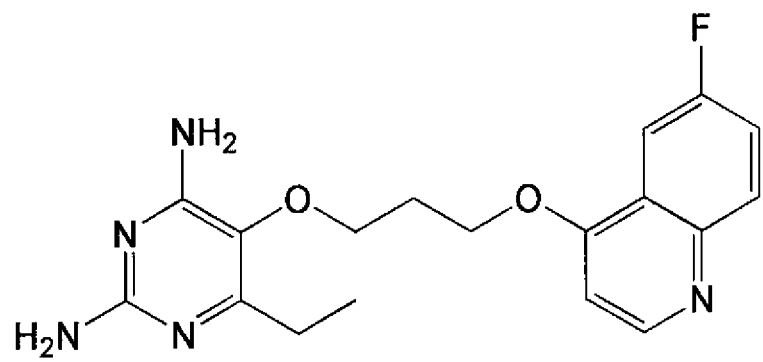
FIG. 3 illustrates the chemical structure of P153.

2,4-diamino-6-ethyl-5-(3-(6-fluoro-quinolin-4-yloxy)propoxy)pyrimidine (P153) (See FIG. 3)

a) 3-(6-fluoroquinolin-4-yloxy)propyl bromide hydrobromide

To a suspension solution of 6-fluoroquinolin-4-ol (3.67 g, 22.5 mmol) (synthesized in overall yield of 32% starting from 4-fluoroaniline and diethyl ethoxymethylenemalonate according to a literature procedure (see Price et al., *Organic Syntheses*, Coll. Vol. 3, p. 272; Vol. 28, p. 38), triphenylphosphine (6.56 g, 25 mmol), and 3-bromo-1-propanol (2.3 mL, 25 mmol) in dry tetrahydrofuran (30 mL) was added diisopropyl azodicarboxylate (4.9 mL, 25 mmol) at 25° C. over 30 minutes under nitrogen and the reaction mixture was left stirring for one hour. Hydrobromic acid (2.8 mL of 48% aqueous solution, 25 mmol) was added, resulting in precipitation of the titled compound. The product was collected by suction filtration and washed with THF, acetone and ether to give a light yellow crystalline solid (4.17 g, 51%). $^1$H NMR (400 MHz, DMSO-d$_6$): 2.45 (2H, m), 3.82 (2H, t, J=6.5 Hz), 4.61 (2H, t, J=5.7 Hz), 7.64 (1H, d, J=6.6 Hz), 8.40 (1H, dt, J=8.5, 2.7 Hz), 7.90 (m, 1H), 8.27 (1H, dd, J=9.4, 4.8 Hz), 9.24 (1H, d, J=6.6 Hz).

b) 2,4-diamino-6-ethyl-5-(3-(6-fluoroquinolin-4-yloxy)propoxy)pyrimidine 2,4-Diamino-6-ethyl-5-hydroxypyrimidine (3.00 g, 19.5 mmol) was added to a stirred solution of lithium hydroxide monohydrate (1.74 g, 41.50 mmol) in DMF (5 mL) and the reaction mixture was stirred at 25° C. for 1 hour. A solution of 3-(6-fluoroquinolin-4-yloxy)propyl bromide [prepared in quantitative yield by treatment of 3-(6-fluoroquinolin-4-yloxy)propyl bromide hydrobromide (4.17 g, 11.4 mmol, step b) with excess of saturated aqueous NaHCO$_3$ solution followed by extraction with dichloromethane and evaporation] in DMF (5 mL) was added and the reaction mixture was left stirring at 25° C. overnight. Addition of water caused precipitation of the product, which was collected by filtration. Recrystallization from MeOH—H$_2$O afforded the free base as a light yellow crystalline solid (3.23 g, 79%). $^1$H NMR (400 MHz, DMSO-d$_6$): 0.88 (3H, t, J=7.6 Hz), 2.25 (2H, q, J=7.6 Hz), 2.29 (2H, m), 3.84 (2H, t, J=5.8 Hz), 4.43 (2H, t, J=5.7 Hz), 5.54 (2H, s), 6.11 (2H, s), 7.10 (1H, d, J=5.2 Hz), 7.63 (H, dt, J=8.7, 2.6 Hz), 7.78 (1H, dd, J=9.6, 2.7 Hz), 8.01 (1H, dd, J=9.2, 5.4 Hz), 8.71 (1H, d, J=5.2 Hz).

c) 2,4-diamino-6-ethyl-5-(3-(6-fluoroquinolin-4-yloxy)propoxy)pyrimidine dihydrochloride To a suspension of 2,4-diamino-6-ethyl-5-(3-(6-fluoroquinolin-4-yloxy)propoxy)pyrimidine (10.02 g, 28 mmol) in methanol (40 mL) was added 5.3 mL of concentrated HCl. The titled compound precipitated almost immediately and was obtained as a white crystalline solid after suction filtration followed by washing with acetone and air-dried (11.81 g, 98%, m.p. 212-214° C.). $^1$H NMR (400 MHz, DMSO-$d_6$): 1.05 (3H, t, J=7.4 Hz), 2.40 (2H, m), 2.48 (2H, m), 3.98 (2H, t, J=5.8 Hz), 4.68 (2H, t, J=5.5 Hz), 7.50 (bs, 2H), 7.60 (1H, d, J=6.5 Hz), 7.90 (1H, s), 8.04 (1H, dt, J=9.0, 2.6 Hz), 8.10 (1H, dd, J=8.9, 2.3 Hz), 8.33 (1H, s), 8.43 (1H, dd, J=9.3, 4.8 Hz), 9.17 (1H, d, J=6.4 Hz), 12.70 (1H, s).

Example 4

Figure 4:
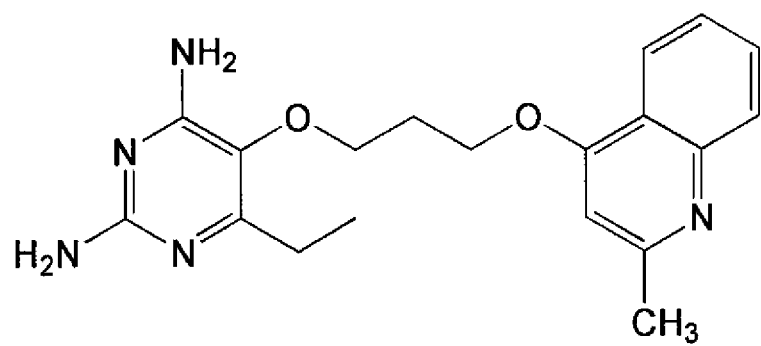
FIG. 4 illustrates the chemical structure of P154.

2,4-diamino-6-ethyl-5-(3-(2-methylquinolin-4-yloxy)propoxy)pyrimidine P154) (See FIG. 4)

a) 3-(2-methylquinolin-4-yloxy)propyl bromide

A mixture of 2-methylquinolin-4-ol (1.59 g, 10 mmol) (synthesized from aniline and acetoacetic ester according to a procedure known in the art: see Leonard et al. (1946) *J. Am. Chem. Soc.* 68:1279-1281), 1,3-dibromopropane (8.08 g, 40 mmol) and potassium carbonate (1.659 g, 12 mmol) in acetone (50 mL) was refluxed until the starting material disappeared. The reaction mixture was filtered and after evaporation of solvent residue was purified by column chromatography on silica gel (1% MeOH: 99% $CH_2Cl_2$ as eluent). The product was obtained as light yellow solid (1.793 g, 64%). $^1$H NMR (400 MHz, $CDCl_3$): 2.48 (2H, m), 2.69 (3H, s), 3.69 (2H, t, J=6.3 Hz), 4.33 (2H, t, J=5.8 Hz), 6.6 (1H, s), 7.43 (1H, t, J=7.5 Hz), 7.66 (1H, t, J=7.8 Hz), 7.95 (1H, d, J=8.5 Hz), 8.12 (1H, d, J=8.3 Hz).

b) 2,4-diamino-6-ethyl-5-(3-(2-methylquinolin-4-yloxy)propoxy)pyrimidine

A mixture of 2,4-diamino-6-ethyl-5-hydroxypyrimidine (0.539 g, 3.5 mmol) and lithium hydroxide monohydrate (0.294 g, 7.0 mmol) in DMF (10 mL) was stirred at 25° C. for 1 hour after that 3-(2-methylquinolin-4-yloxy)propyl bromide (0.980 g, 3.5 mmol) was added to the reaction mixture and the reaction mixture was left to stir at 25° C. overnight. Two thirds of the DMF was evaporated under vacuum and the reaction mixture was poured in water, solid was separated by filtration and dried in oven at 80° C. The crude product was purified by column chromatography on silica gel (4% MeOH: 96% $CH_2Cl_2$ as eluent) to obtain title compound as light yellow solid (0.5814 g, 47%). $^1$H NMR (400 MHz, DMSO-$d_6$): 0.90 (3H, t, J=7.6 Hz), 2.30 (4H, m), 2.60 (3H, s), 3.86 (2H, t, J=5.9 Hz), 4.41 (2H, t, J=5.9 Hz), 5.59 (2H, s), 6.16 (2H, s), 6.97 (1H, s), 7.46 (1H, t, J=7.7 Hz), 7.67 (1H, t, J=7.7 Hz), 7.84 (1H, d, J=8.4 Hz), 8.09 (1H, d, J=8.2 Hz).

c) 2,4-diamino-6-ethyl-5-(3-(2-methylquinolin-4-yloxy)propoxy)pyrimidine monohydrochloride To a stirring suspension of 2,4-diamino-6-ethyl-5-(3-(2-methylquinolin-4-yloxy)propoxy)pyrimidine (0.353 g, 1 mmol) in methanol (10 mL) was added one equivalent of hydrochloric acid at 25° C. After evaporation of solvent and trituration with diethyl ether, product was obtained as light yellow solid (0.3587 g, 92%). mp: 194-196° C. (dec.). $^1$H NMR (400 MHz, DMSO-$d_6$): 0.99 (3H, t, J=7.5 Hz), 2.36 (2H, m), 2.44 (2H, q, J=7.5 Hz), 2.65 (3H, s), 3.97 (2H, t, J=6.0 Hz), 4.45 (2H, t, J=5.6 Hz), 7.09 (1H, s), 7.40 (2H, bs), 7.54 (2H, t, J=7.5 Hz), 7.75 (1H, t, J=7.8 Hz), 7.93 (2H, m), 8.14 (2H, m), 12.55 (1H, bs).

Example 5

Figure 5:
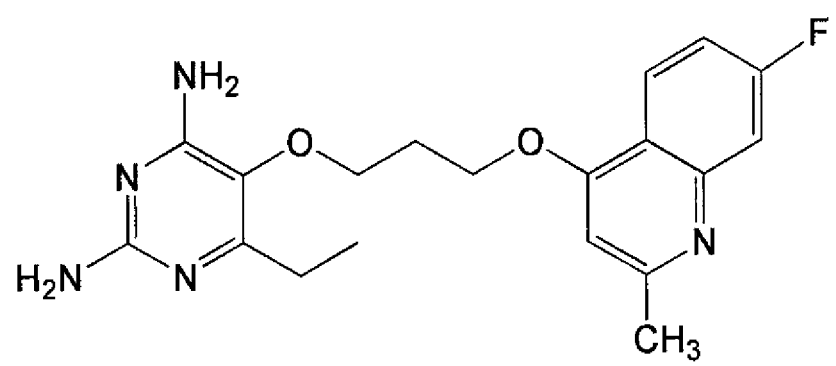
FIG. 5 illustrates the chemical structure of P157.

2,4-diamino-6-ethyl-5-(3-(7-fluoro-2-methylquinolin-4-yloxy)propoxy)pyrimidine (P157) (See FIG. 5)

a) 7-fluoro-2-methylquinolin-4-ol

To a stirring solution of 3-fluoroaniline (4.44 g, 40 mmol) and acetoacetic ester (5.20 g, 40 mmol), a catalytic amount (2 drops) of dilute hydrochloric acid was added at 25° C., within 10 minutes water began to separate and small amount of heat was generated. The reaction mixture was allowed to stand at 25° C. overnight; the reaction mixture was diluted with dichloromethane (150 mL), washed successively with 0.5 N HCl (2×50 mL), 0.5 N NaOH (2×50 mL) and water, dried over anhydrous sodium sulphate. Dichloromethane was evaporated and oily residue was added to the refluxing diphenyl ether (40 mL) over a period of 5 minutes, refluxing was continued for 1 hour after that reaction mixture was cooled at 25° C. and solid was separated by filtration, washed with diethyl ether to remove some coloring impurities. The product was obtained as yellow solid (2.3388 g, 33%, based on 3-fluoroaniline) as isomeric mixture of 5 and 7-fluoro-2-methylquinolin-4-ol, used in the next step without purification.

b) 3-(7-fluoro-2-methylquinolin-4-yloxy)propyl bromide

A mixture of 5- and 7-fluoro-2-methylquinolin-4-ol (2.12 g, 12 mmol), 1,3-dibromopropane (9.70 g, 48 mmol) and anhydrous potassium carbonate (1.99 g, 14.4 mmol) in acetone (60 mL) was refluxed until the starting material disappeared. The reaction mixture was filtered and after the evaporation of solvent, residue was purified by column chromatography on silica gel (1% MeOH:99% $CH_2Cl_2$ as eluent). 3-(7-Fluoro-2-methylquinolin-4-yloxy)propyl bromide was separated as slightly yellow solid (1.25 g, 35%), the rest of the compound was obtained as isomeric mixture (0.89 g, 25%). $^1$H NMR (400 MHz, $CDCl_3$): 2.47 (2H, m), 2.68 (3H, s), 3.67 (2H, t, J=6.3 Hz), 4.33 (2H, t, J=5.8 Hz), 6.62 (1H, s), 7.20 (1H, dt, J=8.6, 2.4 Hz), 7.57 (1H, dd, J=10.5, 2.4 Hz), 8.10 (1H, dd, J=9.1, 6.2 Hz).

c) 2,4-diamino-6-ethyl-5-(3-(7-fluoro-2-methylquinolin-4-yloxy)propoxy)pyrimidine A mixture of 2,4-diamino-6-ethyl-5-hydroxypyrimidine (0.5395 g, 3.5 mmol) and lithium hydroxide monohydrate (0.294 g, 7.0 mmol) in DMF (10 mL) was stirred at 25° C. for 1 hour after that 3-(7-fluoro-2-methylquinolin-4-yloxy)propyl bromide (1.043 g, 3.5 mmol) was added to the reaction mixture and the reaction mixture was left to stir at 25° C. overnight. Two thirds of the DMF was evaporated under vacuum and reaction mixture was poured in water, solid was separated by filtration and dried in oven at 80° C. The crude product was purified by column chromatography on silica gel (4% MeOH: 96% $CH_2Cl_2$ as eluent). The product was obtained as white crystalline solid (0.6629 g, 51%). $^1$H NMR (400 MHz, DMSO-$d_6$): 0.89 (3H, t, J=7.5 Hz), 2.28 (4H, m), 2.60 (3H, s), 3.85 (2H, t, J=5.9 Hz), 4.42 (2H, t, J=5.9 Hz), 5.57 (2H, s), 6.15 (2H, s), 6.99 (1H, s), 7.39 (1H, dt, J=8.8, 2.5 Hz), 7.57 (1H, dd, J=10.8, 2.5 Hz), 8.15 (1H, dd, J=9.1, 6.4 Hz).

d) 2,4-diamino-6-ethyl-5-(3-(7-fluoro-2-methylquinolin-4-yloxy)propoxy)pyrimidine monohydrochloride To a stirring suspension of 2,4-diamino-6-ethyl-5-(3-(7-fluoro-2-methylquinolin-4-yloxy)propoxy)pyrimidine (0.3714 g, 1 mmol) in methanol (10 mL) was added one equivalent of hydrochloric acid at 25° C. After evaporation of solvent and trituration with diethyl ether, product was obtained as white crystalline solid (0.3834 g, 94%). m.p. >200° C., $^1$H NMR (400 MHz, DMSO-d$_6$): 0.99 (3H, t, J=7.6 Hz), 2.35 (2H, m), 2.44 (2H, q, J=7.6 Hz), 2.64 (3H, s), 3.97 (2H, t, J=5.8 Hz), 4.45 (2H, t, J=5.5 Hz), 7.07 (1H, s), 7.45 (3H, m), 7.64 (1H, d, J=10.5 Hz), 7.90 (1H, bs), 8.19 (1H, dd, J=8.9, 6.3 Hz), 8.33 (1H, bs), 12.30 (1H, bs).

Example 6

6: 2,4-diamino-6-ethyl-5-(3-(1-indolyl)propoxy) pyrimidine monohydrochloride

A representative procedure for the preparation of 2,4-diamino-6-ethyl-5-(3-(1-indolyl)propoxy)pyrimidine monohydrochloride is provided below:
a) 1-(3-bromopropyl)indole A solution of indole (1.17 g, 10 mmol) in anhydrous DMF (5 mL) at 0° C. was added to a suspension of sodium hydride (0.48 g, 11 mmol, 55%) in anhydrous DMF (3 mL). The reaction mixture was stirred at 25° C. for 30 minutes. 1-3-Dibromopropane (2.04 mL, 20 mmol) was added at 0° C. and the reaction was stirred at 0° C. until the starting material has been consumed. The reaction was neutralized with diluted HCl and extracted with ethyl acetate and evaporated. The crude product was purified by column chromatography on SiO$_2$ with 10% ethyl acetate in hexane as eluent. The product was obtained as a light yellow oil (0.9048 g, 38%). $^1$H NMR (400 MHz, CDCl$_3$), 2.38 (2H, m), 3.34 (2H, t, J=6.1 Hz), 4.37 (2H, t, J=6.3 Hz), 6.57 (1H, d, J=3.0 Hz), 7.19 (2H, m), 7.28 (1H, m), 7.43 (1H, d) J=8.1 Hz), 7.69 (1H, d, J=7.8 Hz).
b) 2,4-diamino-6-ethyl-5-(3-(1-indolyl)propoxy)pyrimidine 2,4-diamino-6-ethyl-5-hydroxypyrimidine (0.4625 g, 3 mmol) was added to a stirred solution of lithium hydroxide monohydrate (0.3147 g, 7.5 mmol) in DMF (2 mL) and the reaction mixture was stirred for 1 hour. A solution of 1-(3-bromopropyl)indole (0.7144 g, 3 mmol) in DMF (1 mL) was added and the reaction mixture was left stirring at 25° C. overnight. The reaction was diluted with dichloromethane and extracted with water. The dichloromethane layer was evaporated and the residue was recrystallized from aqueous methanol. The product was obtained as a slightly yellow solid (0.4484 g, 48%). $^1$H NMR (DMSO-d$_6$): 1.02 (3H, t, J=7.5 Hz), 2.20 (2H, m), 2.32 (2H, q, J=7.5 Hz), 3.60 (2H, t, J=6.3 Hz), 4.34 (2H, t, J=7.2 Hz), 5.56 (2H, s), 6.07 (2H, s), 6.43 (1H, d, J=3.1 Hz), 7.01 (1H, m), 7.13 (1H, m), 7.40 (1H, d, J=3.1 Hz), 7.50 (1H, d, J=8.3 Hz), 7.54 (1H, d, J=7.8 Hz).
c) 2,4-diamino-6-ethyl-5-(3-(1-indolyl)propoxy)pyrimidine monohydrochloride 2,4-diamino-6-ethyl-5-(3-(1-indolyl)propoxy)pyrimidine (0.1557 g, 0.5 mmol) was suspended in methanol (1 mL) and 1 equivalent of concentrated HCl was added. The titled compound was obtained after evaporation and trituration of the residue with acetonitrile as an off-white crystalline solid (0.1670 g, 96%). $^1$H NMR (DMSO-d$_6$): 1.09 (3H, t, J=7.5 Hz), 2.26 (2H, m), 2.44 (2H, q, J=7.5 Hz), 3.71 (2H, t, J=6.4 Hz), 4.33 (2H, t, J=7.1 Hz), 6.45 (1H, d, J=2.8 Hz), 7.02 (1H, m), 7.14 (1H, m), 7.40 (2H, m), 7.50 (1H, d, J=8.1 Hz), 7.55 (1H, d, J=7.8 Hz), 7.82 (1H, s), 8.32 (1H, s), 12.33 (1H, s).

Example 7

Figure 6:
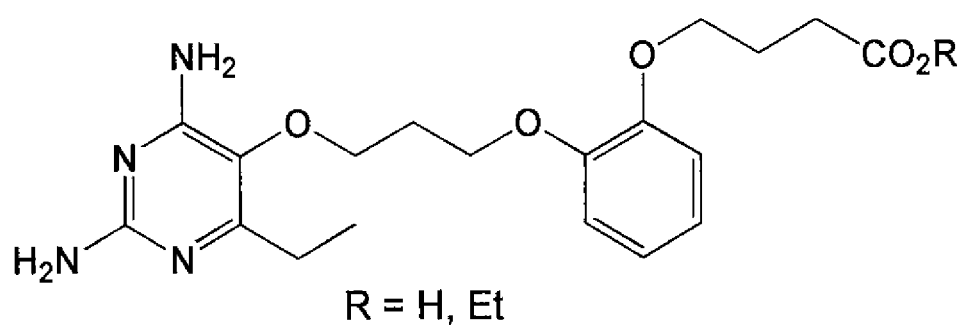
FIG. 6 illustrates the chemical structure of P135 (R=H) and P217 (R=Et).

2,4-diamino-6-ethyl-5-(3-(2-(3-carboxypropoxy) phenoxy)propoxy)pyrimidine (P135) and its ethyl ester (P217) (See FIG. 6)

a) Ethyl 4-(2-hydroxyphenoxy)butanoate

To a solution of pyrocatechol (5.51 g, 50 mmol) in dry DMF (30 mL) was slowly added sodium hydride (1.2 g, 50 mmol) at 0° C. After stirring at 25° C. for 4 hours, the reaction mixture was heated at 65-70° C. for 1 hour followed by an addition of ethyl 4-bromobutyrate (10.7 mL, 75 mmol). The reaction mixture was then left stirring at this temperature for 6 hours. Upon quenching with water, extraction with dichloromethane, and evaporation gave the crude product which was purified by column chromatography, eluting with 87% hexane:10% CH$_2$Cl$_2$:3% EtOAc. Crystallization with hexane afforded a white solid in 55% yield (6.17 g, mp. 37.2-38.4° C.). $^1$H NMR (400 MHz, CDCl$_3$): 1.26 (3H, t, J=7.1 Hz), 2.17 (2H, m), 2.52 (2H, t, J=7.0 Hz), 4.09 (2H, t, J=6.0 Hz), 4.16 (2H, q, J=7.1 Hz), 6.81-6.89 (3H, m), 6.92-6.94 (1H, m).
b) Ethyl 4-(2-(3-bromopropoxy)phenoxy)butanoate To a stirred solution of ethyl 4-(2-hydroxyphenoxy)butanoate (5.61 g, 25 mmol) in DMF (25 mL) at 0° C. was slowly added sodium hydride (0.6 g, 25 mmol) and then the solution was left stirring at 0° C. for 4 hours. To a stirred solution at 65-70° C. was added 1,3-dibromopropane (3.80 mL, 37.5 mmol). The resulting solution was continued to stir at 65-70° C. for 3 hours. Normal work-up and purification by silica gel column chromatography gave bromo-compound as a white solid in 60% yield (5.18 g, m.p. 31-32.6° C., CH$_2$Cl$_2$/hexane). $^1$H NMR (400 MHz, CDCl$_3$): 1.25 (3H, t, J=7.1 Hz), 2.13 (2H, m), 2.34 (2H, m), 2.54 (2H, t, J=7.3 Hz), 3.64 (2H, t, J=6.4 Hz), 4.04 (2H, t, J=6.2 Hz), 4.10-4.15 (4H, m), 6.99-6.93 (4H, m).
c) 2,4-diamino-6-ethyl-5-(3-(2-(3-carboxypropoxy)phenoxy)propoxy)pyrimidine 2,4-Diamino-6-ethyl-5-hydroxypyrimidine (0.4625 g, 3 mmol) was added to a stirred solution of lithium hydroxide monohydrate (0.4406 g, 10.5 mmol) in DMF (4 mL) and the reaction mixture was stirred at 25° C. for 1 hour. A solution of ethyl 4-(2-(3-bromopropoxy)phenoxy)butanoate (1.0357 g, 3 mmol) in DMF (1 mL) was added and the reaction mixture was left stirring at 25° C. overnight. DMF was partially removed under reduced pressure to give residue. The residue was diluted with water and extracted with dichloromethane. The aqueous layer was neutralized with dilute HCl to give white solid. Recrystallization with acetone afforded the desired diaminopyrimidine as white solid (0.6911 g, 59%, m.p. 204-206° C.). $^1$H NMR (400 MHz, DMSO-d$_6$): 1.10 (3H, t, J=7.5 Hz), 1.91 (2H, m), 2.14 (2H, m), 2.31-2.39 (4H, m), 3.78 (2H, t, J=6.1 Hz), 3.96 (2H, t, J=6.4 Hz), 4.13 (2H, t, J=6.1 Hz), 5.60 (2H, s), 6.09 (2H, s), 6.86-6.90 (2H, m), 6.95-7.01 (2H, m).
d) 2,4-diamino-6-ethyl-5-(3-(2-(3-carboxypropoxy)phenoxy)propoxy)pyrimidine hydrochloride To a suspension of 2,4-diamino-6-ethyl-5-(3-(2-(3-carboxypropoxy)phenoxy)propoxy)pyrimidine (0.3904 g, 1 mmol) in water (1 mL) was added one equivalent of concentrated HCl. The titled compound was obtained, after trituration of the reaction mixture with diethyl ether, as a white crystalline solid (0.4055 g, 95%). $^1$H NMR (400 MHz, DMSO-d$_6$): 1.09 (3H, t, J=7.5 Hz), 1.90 (2H, m), 2.18 (2H, m), 2.38 (2H, t, J=7.3 Hz), 2.48 (2H, q, J=7.5 Hz), 3.89 (2H, t, J=6.1 Hz), 3.95 (2H, t, J=6.4 Hz), 4.12 (2H, t, J=6.0 Hz), 6.86-6.90 (2H, m), 6.95-7.02 (2H, m), 7.81 (1H, bs), 8.14 (1H, bs), 8.18 (1H, bs), 12.34 (1H, bs).
e) 2,4-diamino-6-ethyl-5-(3-(2-(3-ethoxycarbonylpropoxy) phenoxy)propoxy)pyrimidine To a solution of 2,4-diamino-6-ethyl-5-(3-(2-(3-carboxypropoxy)phenoxy)propoxy)pyrimidine (0.3904 g, 1 mmol) and a catalytic amount of con. H$_2$SO$_4$ in EtOH (4 mL) was added triethyl orthoformate (2 mL) and the solution was left stirring at 25° C. for 8 hours. The reaction mixture was neutralized with K$_2$CO$_3$ and evaporated to dryness. The crude product was diluted with water and extracted with CH$_2$Cl$_2$.

Evaporation to dryness gave the desired ester as white semisolid (0.2720 g, 65%). $^1$H NMR (500 MHz, DMSO-$d_6$): 0.99 (3H, t, J=7.5 Hz), 1.15 (3H, t, J=7.1 Hz), 1.93 (2H, m), 2.13 (2H, m), 2.33 (2H, q, J=7.5 Hz), 2.45 (2H, t, J=7.3 Hz), 3.78 (2H, t, J=6.0 Hz), 3.95 (2H, t, J=6.3 Hz), 4.03 (2H, q, J=7.1 Hz), 4.13 (2H, t, J=6.0 Hz), 5.54 (2H, s), 6.07 (2H, s), 6.87-6.90 (2H, m), 6.95-7.01 (2H, m).

f) 2,4-diamino-6-ethyl-5-(3-(2-(3-ethoxycarbonylpropoxy)phenoxy)propoxy)pyrimidine hydrochloride To a suspension of 2,4-diamino-6-ethyl-5-(3-(2-(3-ethoxycarbonylpropoxy)phenoxy)propoxy)pyrimidine (0.4185 g, 1 mmol) in EtOH (1 mL) was added one equivalent of concentrated HCl. The titled compound was obtained, after trituration of the reaction mixture with diethyl ether, as a white crystalline solid (0.4322 g, 95%). $^1$H NMR (500 MHz, DMSO-$d_6$): 1.09 (3H, t, J=7.6 Hz), 1.15 (3H, t, J=7.1 Hz), 1.93 (2H, m), 2.18 (2H, m), 2.44 (2H, t, J=7.4 Hz), 2.49 (2H, q, J=7.7 Hz), 3.89 (2H, t, J=6.1 Hz), 3.95 (2H, t, J=6.3 Hz), 4.04 (2H, q, J=7.1 Hz), 4.12 (2H, t, J=5.7 Hz), 6.87-6.90 (2H, m), 6.95-7.01 (2H, m), 7.43 (2H, bs), 7.83 (1H, s), 8.33 (1H, s), 12.39 (1H, s).

Example 8

Figure 7:
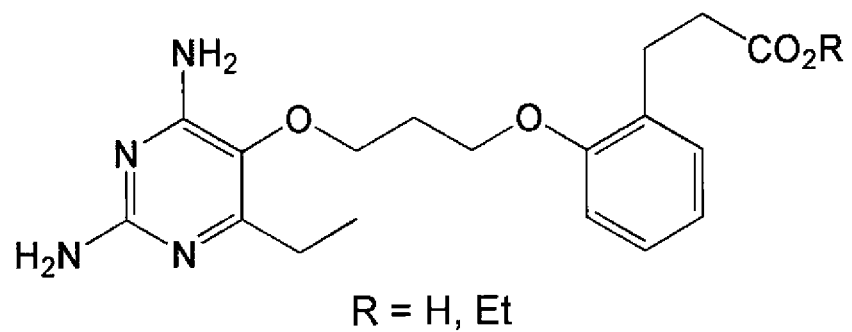
FIG. 7 illustrates the chemical structure of P195 (R=Et) and P218 (R=H).

2,4-diamino-6-ethyl-5-(3-(2-(2-carboxyethyl)phenoxy)propoxy)pyrimidine (P218) and its ethyl ester (P195) (See FIG. 7)

a) Methyl 3-(2-hydroxyphenyl)propanoate

To a stirred solution of dihydrocoumarin (10 mL, 78.9 mmol) and a catalytic amount of conc. $H_2SO_4$ in dry methanol (300 mL) was added and the reaction mixture was then heated at 55° C. for 8 hours. Methanol was evaporated to dryness to give crude product which was subjected to neutralize with $K_2CO_3$. The residue was diluted with water and extracted with dichloromethane. Purification of the crude product by column chromatography (20% $CH_2Cl_2$:3% EtOAc:77% Hexane as eluent) gave the desired ester as colorless oil (12.80 g, 90%). $^1$H NMR (400 MHz, $CDCl_3$): 2.71 (3H, t, J=6.4 Hz), 2.89 (2H, t, J=6.4 Hz), 3.67 (3H, s), 6.83-6.87 (2H, m), 7.06-7.12 (2H, m), b) Methyl 3-(2-(3-bromopropoxy)phenyl)propanoate To a solution of methyl 3-(2-hydroxyphenyl)propanoate (1.80 g, 10 mmol), triphenylphosphine (3.15 g, 12 mmol), and 3-bromo-1-propanol (1.1 mL, 12 mmol) in dry tetrahydrofuran (30 mL) was added diisopropyl azodicarboxylate (2.4 mL 12 mmol) at 25° C. over 20 minutes under nitrogen and the reaction mixture was left stirring for an additional two hours. Upon evaporation of the tetrahydrofuran layer gave the crude product which was subjected to purify by silica gel column chromatography, eluting with a mixture of hexane:$CH_2Cl_2$:EtOAc (8:1.7:0.3). The bromo compound was obtained as yellow oil (2.26 g, 75%). $^1$H NMR (400 MHz, $CDCl_3$): 2.33 (2H, m), 2.58 (2H, t, J=7.8 Hz), 2.92 (2H, t, J=7.8 Hz), 3.61 (2H, t, J=6.4 Hz), 3.65 (3H, s), 4.10 (2H, t, J=5.7 Hz), 6.84 (1H, d, J=8.4 Hz), 6.88 (1H, d, J=7.3 Hz), 7.13-7.19 (2H, m).

c) 2,4-diamino-6-ethyl-5-(3-(2-(2-carboxyethyl)phenoxy)propoxy)pyrimidine 2,4-Diamino-6-ethyl-5-hydroxypyrimidine (0.4625 g, 3 mmol) was added to a stirred solution of lithium hydroxide monohydrate (0.4406 g, 10.5 mmol) in DMF (4 mL) and the reaction mixture was stirred at 25° C. for 1 hour. A solution of methyl 3-(2-(3-bromopropoxy)phenyl)propanoate (0.9035 g, 3 mmol) in DMF (1 mL) was added and the reaction mixture was left stirring at 25° C. overnight. DMF was partially removed under reduced pressure to give residue. The residue was diluted with water followed by extraction with dichloromethane. The aqueous layer was neutralized with dil. HCl to give white solid. Recrystallization from acetone afforded the desired diaminopyrimidine as white solid (0.6271 g, 58%, m.p. 155.5-157.5° C.). $^1$H NMR (400 MHz, DMSO-$d_6$): 1.04 (3H, t, J=7.6 Hz), 2.19 (2H, m), 2.39 (2H, q, J=7.5 Hz), 2.46 (2H, t, J=7.5 Hz), 2.78 (2H, t, J=7.7 Hz), 3.83 (2H, t, J=6.1 Hz), 4.15 (2H, t, J=5.9 Hz), 6.29 (2H, bs), 6.85 (1H, t, J=7.4 Hz), 6.96 (2H, bs), 6.98 (1H, d, J=8.1 Hz), 7.14-7.19 (2H, m).

d) 2,4-diamino-6-ethyl-5-(3-(2-(2-carboxyethyl)phenoxy)propoxy)pyrimidine hydrochloride To a suspension of 2,4-diamino-6-ethyl-5-(3-(2-(2-carboxyethyl)phenoxy)propoxy)pyrimidine (0.3604 g, 1 mmol) in water (1 mL) was added one equivalent of concentrated HCl. The titled compound was obtained, after trituration of the reaction mixture with diethyl ether, as a white crystalline solid (0.3770 g, 95%). $^1$H NMR (400 MHz, DMSO-$d_6$): 1.12 (3H, t, J=7.5 Hz), 2.22 (2H, t, J=5.8 Hz), 2.44-2.52 (4H, m), 2.78 (2H, t, J=7.5 Hz), 3.89 (2H, t, J=5.9 Hz), 4.14 (2H, t, J=5.5 Hz), 6.85 (1H, t, J=7.3 Hz), 6.98 (1H, d, J=8.1 Hz), 7.14-7.19 (2H, m) 7.41 (2H, s), 7.85 (1H, s), 8.31 (1H, s), 12.11 (1H, bs), 12.54 (1H, s).

e) 2,4-diamino-6-ethyl-5-(3-(2-(2-ethoxycarbonylethyl)phenoxy)propoxy)pyrimidine To a solution of 2,4-diamino-6-ethyl-5-(3-(2-(2-carboxyethyl)phenoxy)propoxy)pyrimidine (0.3604 g, 1 mmol) and a catalytic amount of con. $H_2SO_4$ in EtOH (4 mL) was added triethyl orthoformate (2 mL) and the mixture was left stirring at 25° C. for 8 hours. The reaction mixture was neutralized with $K_2CO_3$ and evaporated to dryness. The crude product was diluted with water and extracted with $CH_2Cl_2$. Evaporation to dryness gave the desired ester as white solid (0.3496 g, 90%, mp. 124.5-1255.5° C.). $^1$H NMR (500 MHz, DMSO-$d_6$): 1.24 (3H, t, J=7.3 Hz), 1.26 (3H, t, J=7.7 Hz), 2.26 (2H, m), 2.59 (2H, q, J=7.7 Hz), 2.62 (2H, t, J=7.7 Hz), 2.95 (2H, t, J=7.7 Hz), 3.98 (2H, t, J=6.0 Hz), 4.13 (2H, q, J=7.1 Hz), 4.27 (2H, t, J=5.7 Hz), 5.17 (2H, bs), 5.28 (2H, bs), 6.90 (1H, d, J=8.2 Hz), 6.93 (1H, t, J=7.5 Hz), 7.17 (1H, dd, J=7.4, 1.4 Hz), 7.22 (1H, dt, J=7.8, 1.5 Hz).

f) 2,4-diamino-6-ethyl-5-(3-(2-(2-ethoxycarbonylethyl)phenoxy)propoxy)pyrimidine hydrochloride To a suspension of 2,4-diamino-6-ethyl-5-(3-(2-(2-ethoxycarbonylethyl)phenoxy)propoxy)pyrimidine (0.3885 g, 1 mmol) in EtOH (1 mL) was added one equivalent of concentrated HCl. The titled compound was obtained, after trituration of the reaction mixture with diethyl ether, as a white crystalline solid (0.4037 g, 95%). $^1$H NMR (400 MHz, DMSO-$d_6$): 1.10 (3H, t, J=7.8 Hz), 1.13 (3H, t, J=7.1 Hz), 2.22 (2H, m), 2.47-2.55 (m, 4H), 2.81 (2H, t, J=7.6 Hz), 3.89 (2H, t, J=6.2 Hz) 4.02 (2H, q, J=7.1 Hz), 4.15 (2H, t, J=5.8 Hz), 6.85 (1H, t, J=7.4 Hz), 6.99 (1H, d, J=8.1 Hz), 7.14 (1H, d, J=8.2 Hz), 7.18 (1H, t, J=7.5 Hz), 7.38 (2H, s), 7.85 (1H, bs), 8.14 (1H, s), 12.32 (1H, s).

Example 9

Figure 8:
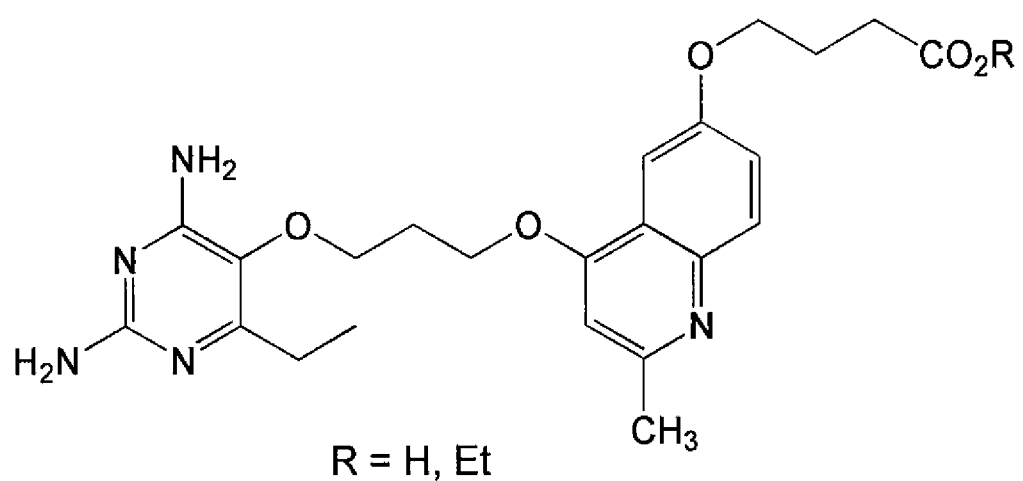
FIG. 8 illustrates the chemical structure of P169 (R=H) and P219 (R=Et).

2,4-diamino-6-ethyl-5-(3-(6-(3-carboxypropoxy-2-methylquinolin-4-yloxy)-propoxy)pyrimidine (P169) and its ethyl ester (P219) (See FIG. 8)

a) 6-(3-Ethoxycarbonylpropoxy)-2-methylquinolin-4-ol

To a stirring mixture of ethyl 4-(4-aminophenoxy)butanoate (3.12 g, 14 mmol) and acetoacetic ester (1.82 g, 14 mmol) was added a catalytic amount of hydrochloric acid and cyclized in refluxing diphenyl ether as described in Example 5a. The product was obtained as a light yellow solid (1.70 g, 42%). $^1$H NMR (400 MHz, DMSO-$d_6$): 1.32 (3H, t, J=7.1 Hz), 2.15 (2H, m), 2.50 (3H, s), 2.62 (2H, t, J=7.3 Hz), 4.21

(4H, m), 6.09 (1H, s), 7.42 (1H, dd, J=9.0, 2.7 Hz), 7.58 (1H, d, J=2.7 Hz), 7.65 (1H, d, J=9.0 Hz), 11.8 (1H, s).

b) 3-(6-(3-Ethoxycarbonylpropoxy)-2-methylquinolin-4-yloxy)propyl bromide

A reaction between 6-(3-ethoxycarbonylpropoxy)-2-methylquinolin-4-ol (1.157 g, 4 mmol), 1,3-dibromopropane (3.230 g, 16 mmol) and anhydrous potassium carbonate (0.663 g, 4.8 mmol) in acetone was performed similar to that described in Example 5b. The expected compound was obtained as a white solid (0.903 g, 55%). $^1$H NMR (400 MHz, CDCl$_3$): 1.25 (3H, t, J=7.2 Hz), 2.18 (2H, m), 2.56 (4H, m), 2.65 (3H, s), 3.67 (2H, t, J=6.3 Hz), 4.14 (4H, m), 4.31 (2H, t, J=5.8 Hz), 6.61 (s, 1H), 7.29 (1H, dd, J=9.1, 2.6 Hz), 7.36 (1H, d, J=2.6 Hz), 7.85 (1H, d, J=9.1 Hz).

c) 2,4-diamino-6-ethyl-5-(3-(6-(3-ethoxycarbonylpropoxy)-2-methylquinolin-4-yloxy)propoxy)pyrimidine A mixture of 2,4-diamino-6-ethyl-5-hydroxypyrimidine (0.308 g, 2.0 mmol), potassium hydroxide (0.123 g, 2.2 mmol) and 3-(6-(3-ethoxycarbonylpropoxy)-2-methylquinolin-4-yloxy)propyl bromide (0.821 g, 2.0 mmol) in DMF was stirred at 25° C. overnight. The DMF was evaporated to dryness and the residue was purified by column chromatography over silica gel (4% MeOH: 96% CH$_2$Cl$_2$ as eluent). The product was obtained as a light yellow solid (0.3578 g, 37%). $^1$H NMR (400 MHz, DMSO-d$_6$): 0.90 (3H, t, J=7.5 Hz), 1.16 (3H, t, J=7.1 Hz), 2.08 (2H, m), 2.28 (4H, m), 2.48 (2H, t, J=7.0 Hz), 2.56 (3H, s), 3.86 (2H, t, J=5.8 Hz), 4.06 (4H, m), 4.41 (2H, t, J=5.8 Hz), 5.53 (2H, s), 6.11 (2H, s) 6.93 (1H, s), 7.31 (1H, dd, J=9.1, 2.6 Hz), 7.37 (1H, d, J=2.6 Hz), 7.76 (1H, d, J=9.1 Hz).

d) 2,4-diamino-6-ethyl-5-(3-(6-(3-carboxypropoxy)-2-methylquinolin-4-yloxy)propoxy)pyrimidine A suspension of the ethyl ester obtained in step (c) (0.314 g, 0.65 mmol) and aqueous KOH solution (10 equiv) was stirred at 25° C. overnight. The solution was neutralized by addition of dilute HCl. The precipitate formed was separated by filtration and dried in an oven at 80° C. to give a light yellow solid (0.2487 g, 84%). $^1$H NMR (400 MHz, DMSO-d$_6$): 0.91 (3H, t, J=7.5 Hz), 1.98 (2H, m), 2.29 (4H, m), 2.41 (2H, t, J=7.2 Hz), 2.56 (3H, s), 3.86 (2H, t, J=5.5 Hz), 4.05 (2H, t, J=5.9 Hz), 4.40 (2H, t, J=5.3 Hz), 5.67 (2H, s), 6.24 (2H, s) 6.94 (1H, s), 7.33 (2H, m), 7.75 (1H, d, J=9.1 Hz).

e) 2,4-diamino-6-ethyl-5-(3-(6-(3-ethoxycarbonylpropoxy)-2-methylquinolin-4-yloxy)propoxy)pyrimidine monohydrochloride To a stirring suspension of 2,4-diamino-6-ethyl-5-(3-(6-(3-ethoxycarbonylpropoxy)-2-methylquinolin-4-yloxy)propoxy)pyrimidine obtained from step (c) (0.179 g, 0.37 mmol) in ethanol (0.5 mL) was added one equivalent of hydrochloric acid at 25° C. After evaporation of solvent and trituration with acetone, the product was obtained as white crystalline solid (0.117 g, 61%). $^1$H NMR (400 MHz, DMSO-d$_6$): 0.90 (3H, t, J=7.5 Hz), 1.15 (3H, t, J=7.0 Hz), 2.00 (2H, m), 2.35 (4H, m), 2.40 (2H, m), 2.70 (3H, s), 3.85 (2H, t, J=6.0 Hz), 4.02 (2H, q, J=7.0 Hz), 4.10 (2H, t, J=6.0 Hz), 4.52 (2H, m), 7.25 (s, 1H), 7.42 (3H, m), 7.90 (1H, bs), 8.00 (1H, d, J=10 Hz), 8.30 (1H, bs).

f) 2,4-diamino-6-ethyl-5-(3-(6-(3-carboxypropoxy)-2-methylquinolin-4-yloxy)propoxy)pyrimidine monohydrochloride The compound was synthesized similar to (e). After evaporation of solvent and trituration with acetone, the product was obtained as white crystalline solid in quantitative yield. $^1$H NMR (400 MHz, DMSO-d$_6$): 1.00 (3H, t, J=7.5 Hz), 1.99 (2H, m), 2.37 (2H, m), 2.41 (4H, m), 2.63 (3H, s), 3.97 (2H, t, J=6.0 Hz), 4.02 (2H, q, J=−7.0 Hz), 4.08 (2H, t, J=6.0 Hz), 4.45 (2H, t, J=5.3 Hz), 7.07 (s, 1H), 7.40 (3H, m), 7.86 (1H, d, J=9.0 Hz), 7.90 (1H, bs), 8.00 (1H, d, J=10 Hz), 8.25 (1H, bs).

Example 10

Compound Design Principle

The compounds were designed by an iterative method based on consideration of the following compound properties: interaction with the target enzyme (i.e., Plasmodial DHFR) modeled using experimentally derived crystal structures, antimalarial activities in vitro and in vivo, metabolic stability, oral bioavailability and pharmacokinetic properties. The structures of specific compounds complexed with the wild-type and the quadruple mutant enzyme were determined through X-ray diffraction via a known procedure (see Yuvaniyama et al., (2003) *Nat. Struct. Biol.* 10:357-365). This process provides spatial and electronic information about the DHFR active site that was used in the design and optimization of chemical compounds with high affinity and specificity for wild type and quadruple mutant *P. falciparum* DHFR. Using iterative cycles, new designed inhibitors could be synthesized, co-crystallized with the DHFR enzyme and studied using x-ray diffraction to provide an experimental determination of exactly how each compound binds at the DHFR active site. Based on these data, structural modifications of the inhibitor can then be made to further enhance binding to the target enzyme. This led to the understanding of the basic requirements that are needed for effective binding of the compounds to the active site of the enzyme, i.e., the wild-type and resistant mutant enzyme as described in Example 11 below. The affinities of the compounds for the wild-type and mutant enzymes were measured as $K_i$ values (see Example 12). The inhibitory activities against *Plasmodium falciparum* were measured by an in vitro method (see Example 13). In addition, the cytotoxicity of the compounds was measured and determined to be minimal (see Example 14). In vivo activities of the compounds against *P. chabaudi* AS and ASP (i.e. pyrimethamine sensitive and pyrimethamine resistant strains respectively) were also measured following oral administration (see Example 15). The bioavailability of the compounds in rats and mice were measured in Example 16. The obtained results were then considered together in order to optimize the properties of the compounds: high binding affinity to wild type and mutant DHFR enzymes (low $K_i$ value), effective antimalarial activities against both *P. falciparum* in vitro, specially the antifolate resistant parasites (low $IC_{50}$ value) and *P. chabaudi* in vivo (low $ED_{90}$ value), and good oral bioavailability of the compounds.

Example 11

Basic Requirements of Effective Compounds

The compounds were designed such that they have the general formula of Het-X—R (I), where —X—R is a flexible side chain of a heterocyclic ring selected from pyrimidine, 1,3,5-triazine, quinazoline, and saturated or partially saturated analogues thereof. The flexibility was needed so that any steric hindrance between the side chain and the mutated residue at position 108 (serine to asparagine) of the mutant enzyme could be avoided. Moreover, other mutations caused further changes in the active site which required further optimization of the side chain. The compounds with good affini-

Example 12

Enzyme Inhibitory Activities

The present invention provides 2,4-diaminopyrimidine derivative compounds, and pharmaceutically acceptable salts thereof, for inhibiting dihydrofolate reductase (DHFR) enzymes of *P. falciparum* including, wild type (WT), double mutants (C59R+S108N), triple mutants (N51I+C59R+S108N, C59R+S108N+I164L), and quadruple mutants (N51I+C59R+S108N+I164L). WT, double-, triple-, and quadruple mutants were prepared with the help of an *E. coli* expression system (*E. coli* BL21(DE3)pLysS) containing the corresponding genes. The activity of the enzymes was determined spectrophotometrically at 25° C. The reaction (1 mL) contained 1×DHFR buffer (50 mM TES, pH 7.0, 75 mM β-mercaptoethanol, 1 mg/mL Bovine Serum Albumin), 100 μM each of the substrate dihydrofolate and cofactor NADPH, and appropriate amount of affinity-purified enzyme to initiate the reaction (0.001-0.005 units in phosphate buffer containing 50 mM KCl).

The inhibition of the various enzymes (e.g., WT, double-, triple-, and quadruple mutant, supra) by the compounds was investigated in a 96 well plate with 200 μL of the above mixture in the presence of antifolate. The kinetics was followed at 340 nm. The $K_i$ values of the inhibitors for the wild type and mutant enzymes were determined by using the following equation:

$IC50 = K_i(1+([S]/Km))$, where IC50 is the concentration of inhibitor which inhibits 50% of the enzyme activity under the standard assay condition and Km is the Michaelis constant for the substrate dihydrofolate.

The inhibition constants (Ki) of the compounds against the wild type and mutant enzymes of dihydrofolate reductase (DHFR) of *Plasmodium falciparum* (Pf DHFR) are summarized in Table 3 below. Low values of Ki indicate avid binding, consistent with the X-ray co-crystal structures which show optimal interactions between the compounds and the enzyme active sites, including hydrophobic, van de Waals, polar and charge-charge interactions. For example, introduction of a carboxylic side chain provides additional binding with R122 in the active site, thus giving a lower Ki-value than its comparator without a carboxylic side chain.

TABLE 3

Inhibition Constants ($K_i$) of 2,4-diaminopyrimidine derivative compounds for binding with wild type and mutant Pf DHFRs.

| | $K_i$-Pf DHFR (nM) | | | | |
|---|---|---|---|---|---|
| Examples | WT | C59R + S108N | N51I + C59R + S108N | C59R + S108N + I164L | N51I + C59R + S108N + I164L |
| pyrimethamine | 0.6 ± 0.2 | 53.9 ± 6.5 | 67.1 ± 4.2 | 112.37 ± 17.49 | 385.0 ± 163.0 |
| P65 | 0.49 ± 0.1 | 3.15 ± 0.13 | 2.61 ± 0.22 | 4.21 ± 0.23 | 5.59 ± 0.1 |
| P111 | 0.92 ± 0.13 | 1.23 ± 0.12 | 1.20 ± 0.05 | 5.02 ± 0.44 | 4.07 ± 0.72 |
| P112 | 1.49 ± 0.13 | 2.22 ± 0.37 | 3.27 ± 0.21 | 2.86 ± 0.62 | 4.61 ± 0.38 |
| P113 | 1.21 ± 0.17 | 1.86 ± 0.11 | 1.82 ± 0.17 | 3.06 ± 0.21 | 4.33 ± 0.28 |
| P134 | 1.19 ± 0.12 | nd | nd | nd | 3.04 ± 0.27 |
| P138 | 1.05 ± 0.07 | 1.45 ± 0.23 | 1.62 ± 0.13 | 1.96 ± 0.17 | 2.66 ± 0.46 |
| P139 | 1.07 ± 0.14 | 1.61 ± 0.41 | 1.67 ± 0.17 | 1.59 ± 0.22 | 2.47 ± 0.33 |
| P140 | 0.92 ± 0.11 | 1.74 ± 0.03 | 3.10 ± 0.38 | 4.12 ± 0.19 | 4.44 ± 0.66 |
| P141 | 1.07 ± 0.07 | 1.31 ± 0.06 | 1.63 ± 0.06 | 2.46 ± 0.16 | 3.90 ± 0.22 |
| P142 | 1.24 ± 0.10 | 2.50 ± 0.19 | 2.03 ± 0.10 | 3.86 ± 0.31 | 4.29 ± 0.48 |
| P144 | 0.84 ± 0.05 | 3.22 ± 0.54 | 2.04 ± 0.21 | 2.44 ± 0.31 | 3.26 ± 0.58 |
| P145 | 1.04 ± 0.03 | 2.30 ± 0.31 | 2.37 ± 0.19 | 3.52 ± 0.62 | 3.81 ± 0.03 |
| P147 | 0.88 ± 0.10 | 2.19 ± 0.15 | 2.25 ± 0.22 | 3.16 ± 0.21 | 4.68 ± 0.33 |
| P149 | 1.05 ± 0.18 | 2.37 ± 0.16 | 3.40 ± 0.15 | 3.66 ± 0.48 | 4.23 ± 1.06 |
| P153 | 1.41 ± 0.13 | nd | nd | nd | 3.41 ± 0.27 |
| P154 | 1.29 ± 0.14 | nd | nd | nd | 4.80 ± 0.36 |
| P155 | 1.17 ± 0.08 | nd | nd | nd | 3.39 ± 0.08 |
| P156 | 1.00 ± 0.15 | nd | nd | nd | 2.83 ± 0.16 |
| P157 | 1.26 ± 0.24 | nd | nd | nd | 3.95 ± 0.06 |
| P163 | 0.47 ± 0.06 | nd | nd | nd | 1.89 ± 0.35 |
| P164 | 0.65 ± 0.09 | nd | nd | nd | 2.60 ± 0.43 |
| P165 | 0.76 ± 0.03 | nd | nd | nd | 1.72 ± 0.11 |
| P166 | 0.42 ± 0.06 | nd | nd | nd | 1.98 ± 0.09 |
| P167 | 0.44 ± 0.04 | nd | nd | nd | 1.11 ± 0.12 |
| P168 | 0.29 ± 0.02 | nd | nd | nd | 0.51 ± 0.06 |
| P170 | 0.25 ± 0.07 | nd | nd | nd | 0.42 ± 0.04 |
| P171 | 0.30 ± 0.07 | nd | nd | nd | 0.62 ± 0.11 |
| P172 | 0.26 ± 0.03 | nd | nd | nd | 0.85 ± 0.03 |
| P135 | 0.72 ± 0.03 | 0.98 ± 0.003 | 1.20 ± 0.05 | 2.54 ± 0.04 | 3.47 ± 0.09 |
| P217 | 0.69 ± 0.10 | nd | nd | nd | 3.30 ± 0.52 |
| P218 | 0.43 ± 0.07 | nd | nd | nd | 0.54 ± 0.12 |
| P195 | 0.26 ± 0.02 | nd | nd | nd | 1.88 ± 0.13 |
| P169 | 0.15 ± 0.04 | nd | nd | nd | 0.36 ± 0.01 |
| P219 | 0.52 ± 0.08 | nd | nd | nd | 1.25 ± 0.22 | nd = not determined

Example 13

In Vitro Activity Against *P. falciparum*

The invention provides 2,4-diaminopyrimidine derivative compounds for treatment of malaria, including non-resistant and drug-resistant malaria. The compounds can be used alone or in combination with sulfonamides, which act on the DHPS enzyme in the folate biosynthetic pathway, and/or other agents which may act through a non-antifolate mechanism. P. falciparum strains were maintained continuously in human erythrocytes at 37° C. under 3% $CO_2$ in standard RPMI 1640 culture media supplemented with 25 mM HEPES, pH 7.4, 0.2% $NaHCO_3$, 40 µg/mL gentamicin and 10% human serum (Trager et al., (1976) Science 193: 673-675). In vitro antimalarial activity was determined by using the [$^3$H]-hypoxanthine incorporation method (Desjardins et al., (1979) Antimicrob. Agents Chemother. 16:710-718), which measures parasite growth through accumulation of a metabolic precursor, hypoxanthine. The compounds were initially dissolved in DMSO and diluted with the same standard culture media Aliquots (25 µL) of the drug of different concentrations were dispensed in 96-well plates and 200 µL of 1.5% cell suspension of parasitized erythrocytes containing 1-2% parasitemia were added. The final concentration of DMSO (0.1%) did not affect the parasite growth. The mixtures were incubated in a 3% $CO_2$ incubator at 37° C. After 24 h of incubation, 25 µL (0.25 µCi) of [$^3$H]-hypoxanthine were added to each well. The parasite cultures were further incubated under the same condition for 18-20 hours. DNA of parasites was harvested onto glass filter paper. The filters were air-dried and 20 µL liquid scintillation fluid was added. The radioactivity on the filters was then measured using a microplate scintillation counter. The concentration of inhibitor which inhibited 50% of the parasite growth ($IC_{50}$) was determined from the sigmoid curve obtained by plotting the percentages of [$^3$H]-hypoxanthine incorporation against drug concentrations. Examples of the compounds in this series with active antimalarial activity against wild type DHFR and, in particular, against parasites carrying single-, double-, triple-, and quadruple mutant DHFR enzymes are shown in Table 3 above.

Table 4 below shows the results obtained with the following mutant strains: K1CB1 (C59R+S108N), W2 (N51I+ C59R+S108N), Csl-2 (C59R+S108N+I164L) and V1/S (N51I+C59R+S108N+I164L).

TABLE 4

Anti-plasmodial activities ($IC_{50}$) of 2,4-diaminopyrimidine derivative compounds against P. falciparum carrying various DHFR types: TM4/8.2 (wild type), K1CB1 (C59R + S108N), W2 (N51I + C59R + S108N), Csl-2 (C59R + S108N + I164L), and V1/S (N51I + C59R + S108N + I164L).

| Compound | $IC_{50}$-P. falciparum (µM) | | | | |
|---|---|---|---|---|---|
| | TM4/8.2 (WT) | K1CB1 | W2 | Csl-2 | V1/S |
| Chloroquine | 0.027 | 0.37 | 0.32 | 0.40 | 0.38 |
| Dihydroartemisinin (nM) | 1.69 ± 0.39 | 1.0 ± 0.57 | 0.59 | 1.1 ± 0.4 | 1.4 |
| Pyr | 0.058 ± 0.03 | >50 | 39.88 | nd | >100 |
| P065 | 0.35 ± 0.08 | 2.63 ± 0.98 | 1.43 ± 0.73 | 3.10 | 5.05 ± 0.47 |
| P111 | 0.025 ± 0.018 | 0.4 ± 0.08 | 2.28 ± 0.9 | nd | 4.83 ± 0.18 |
| P112 | 0.0013 ± 0.000 | 0.02 ± 0.01 | 0.021 ± 0.01 | nd | 0.07 ± 0.02 |
| P113 | 0.004 ± 0.003 | 0.026 ± 0.01 | 0.013 ± 0.01 | nd | 0.050 ± 0.01 |
| P134 | 0.0050 ± 0.001 | 0.038 ± 0.01 | 0.042 ± 0.01 | 0.23 ± 0.10 | 0.41 ± 0.43 |
| P138 | 0.007 ± 0.003 | 0.018 ± 0.001 | 0.033 ± 0.02 | 0.028 ± 0.01 | 0.024 ± 0.002 |
| P139 | 0.0022 ± 0.001 | 0.015 ± 0.003 | 0.011 ± 0.01 | 0.011 ± 0.01 | 0.0049 ± 0.003 |
| P140 | 0.0027 ± 0.001 | 0.015 ± 0.01 | 0.024 ± 0.01 | 0.042 ± 0.005 | 0.055 ± 0.02 |
| P141 | 0.0003 ± 0.000 | 0.00064 ± 0.0003 | 0.0042 ± 0.003 | 0.0037 ± 0.0016 | 0.0055 ± 0.004 |
| P142 | 0.0023 ± 0.001 | 0.0040 ± 0.003 | 0.005 ± 0.0036 | 0.0046 ± 0.003 | 0.0068 ± 0.003 |
| P144 | 0.0017 ± 0.0008 | 0.039 ± 0.01 | 0.058 ± 0.02 | 0.31 ± 0.18 | 0.33 ± 0.14 |
| P145 | 0.0051 ± 0.003 | 0.061 ± 0.02 | 0.18 ± 0.07 | 0.36 ± 0.12 | 0.23 ± 0.13 |
| P147 | 0.0027 ± 0.002 | 0.0065 ± 0.003 | 0.011 ± 0.0004 | 0.01 ± 0.005 | 0.019 ± 0.008 |
| P149 | 0.0032 ± 0.0007 | 0.0040 ± 0.0026 | 0.011 ± 0.01 | 0.028 ± 0.02 | 0.018 ± 0.007 |
| P153 | 0.00025 ± 0.0001 | 0.00065 ± 0.0001 | 0.0012 ± 0.0003 | 0.0014 ± 0.0001 | 0.0046 ± 0.0005 |
| P154 | 0.002 ± .0008 | 0.0057 ± 0.002 | 0.0069 ± 0.002 | 0.028 ± 0.02 | 0.023 ± 0.0045 |
| P155 | 0.0037 ± 0.001 | 0.025 ± 0.01 | 0.016 ± 0.003 | 0.038 ± 0.01 | 0.057 ± 0.005 |
| P156 | 0.0022 ± 0.001 | 0.0062 ± 0.002 | 0.0069 ± 0.003 | 0.021 ± 0.002 | 0.019 ± 0.009 |
| P157 | 0.0024 ± 0.0007 | 0.031 ± 0.01 | 0.007 ± 0.001 | 0.027 ± 0.01 | 0.036 ± 0.01 |
| P163 | 0.0056 ± 0.001 | 0.040 ± 0.03 | 0.089 ± 0.06 | 0.11 ± 0.04 | 0.23 ± 0.11 |
| P164 | 0.0030 ± 0.0008 | 0.024 ± 0.01 | 0.017 ± 0.01 | 0.026 ± 0.002 | 0.068 ± 0.03 |
| P165 | 0.0017 ± 0.0004 | 0.033 ± 0.01 | 0.027 ± 0.0005 | 0.34 ± 0.26 | 0.16 ± 0.08 |
| P166 | 0.0008 ± 0.00004 | 0.023 ± 0.02 | 0.034 ± 0.01 | 0.20 ± 0.12 | 0.14 ± 0.07 |
| P167 | 0.0054 ± 0.001 | 0.0053 ± 0.002 | 0.0038 ± 0.002 | 0.0022 ± 0.001 | 0.005 ± 0.002 |
| P168 | 0.022 ± 0.01 | 0.026 ± 0.03 | 0.033 ± 0.004 | nd | 0.032 ± 0.01 |
| P169 | 0.00022 ± 0.00006 | 0.002 ± 0.0008 | 0.00085 ± 0.0002 | nd | 0.0031 ± 0.002 |
| P170 | 0.043 ± 0.01 | 0.066 ± 0.02 | 0.042 ± 0.02 | nd | 0.056 ± 0.018 |
| P171 | <0.001 | 0.0033 ± 0.001 | 0.0022 ± 0.0005 | nd | 0.017 ± 0.005 |
| P172 | 0.0043 ± 0.001 | 0.052 ± 0.01 | 0.021 ± 0.02 | nd | 0.275 ± 0.04 |
| P135 | 0.0016 ± 0.0006 | 0.0034 ± 0.001 | 0.005 ± 0.001 | 0.024 ± 0.02 | 0.038 ± 0.02 |
| P217 | 0.004 | nd | nd | nd | nd |
| P218 | 0.006 | nd | nd | nd | nd |
| P195 | 0.0025 ± 0.0007 | 0.003 ± 0.0005 | 0.001 ± 0.0005 | 0.014 ± 0.007 | 0.068 ± 0.017 |
| P169 | 0.0003 ± 0.0001 | 0.002 ± 0.0008 | 0.003 ± 0.001 | 0.002 ± 0.0005 | 0.003 ± 0.001 |
| P219 | <0.01 | nd | nd | nd | nd | nd = not determined

Table 4 above shows various 2,4-diaminopyrimidine derivative compounds. Notably, these compounds are very active against pyrimethamine-resistant parasite strains. The $IC_{50}$ values of these examples were far less than that of pyrimethamine against the mutant strains.

Example 14

Determination of Cytotoxicity in Mammalian Cells ($IC_{50}$)

Cytotoxicity tests of the compounds were performed in African green monkey kidney fibroblast (Vero) cells according to the protocol described by Skehan et al., (1990) *J Natl. Cancer Inst.* 82:1107-1112. These compounds have selectivity against malaria parasites with different cytotoxic effect on the mammalian cell line as summarized in Table 5. Compounds with acid and ester have better selectivity against Vero cells than other functional group.

TABLE 5

Cytotoxicity of 2,4-diaminopyrimidine derivative compounds in mammalian cells.

| Example | Cytotoxicity to Vero cells, $IC_{50}$ (μM) | IC50 ratio Vero/TM4 | IC50 ratio Vero/V1/S |
|---|---|---|---|
| Pyr | 32 | 549 | <0.3 |
| P113 | 0.119 | 32 | 2 |
| P153 | 0.037 | 149 | 8 |
| P154 | 0.094 | 38 | 4 |
| P157 | 0.100 | 42 | 3 |
| P135 | >10 | >6000 | >260 |
| P217 | 5.33 | 1380 | nd |
| P218 | >10 | >1620 | nd |
| P195 | 1.25 | 500 | 18 |
| P169 | 0.42 | 1405 | 134 | nd = not determined

Example 15

In Vivo Activity in Rodent Malaria Models

The in vivo anti-malarial activity of the compounds was assessed using the *Plasmodium chabaudi* and *Plasmodium berghei* models by the standard 4-day Peters' test including pyrimethamine as a comparator drug in each experiment. Briefly, 20 gr CD1 male mice (Charles Rivers, UK) were kept in specific pathogen-free conditions and fed ad libitum. For oral administration, compounds were dissolved in standard suspending formula (SSV) [0.5% sodium carboxymethylcellulose, 0.5% benzyl alcohol, 0.4% Tween 80, 0.9% NaCl (all Sigma)] and for intraperitoneal or subcutaneous administration compounds were dissolved in 0.5% w/v hydroxypropylmethylcellulose, 0.4% v/v Tween 80, 0.5% V/v benzyl alcohol in de-ionised water]. Mice were infected intravenously with $4\times10^6$ infected red cells and treated orally (p.o.) with 0.2 ml of a solution of the test compounds two hours (day 0) and on days 1, 2 and 3 post-infection. Parasitaemia was determined by microscopic examination of Giemsa stained blood films taken on day 4. Microscopic counts of blood films from each mouse were processed using GraphPad Prism 4 (GraphPad Software, Inc., CA, USA) and expressed as percentages of inhibition from the arithmetic mean parasitaemias of each group in relation to the untreated group. Compounds were tested in an initial screening at 30 mg/kg/day against *P. chabaudi* AS (non-resistant) over the period described and percentages of inhibition calculated in relation to the untreated controls. Compounds giving 80% inhibition or above were then tested in the same model under a range of doses over the period described in order to obtain dose response curves and calculate their $ED_{50}$ and $ED_{90}$ values. Compounds giving an $ED_{90}$ at or below the level of the comparator (Table 6) were then selected for testing against *P. chabaudi* ASP (pyrimethamine-resistant strain), and in the lethal *P. berghei* ANKA (non-resistant strain). The results of the in vivo tests against *P. chabaudi* AS are summarized in Table 7. From the $ED_{90}$ values is clear that a number of compounds have exquisite activity in this model and are also tested in *P. chabaudi* ASP and *P. berghei* ANKA.

As shown in Table 6, a number of these compounds show $ED_{90}$ values 2-90-fold lower ($ED_{90}$=0.01-0.36 mg/kg) than the existing drug pyrimethamine which displays $ED_{90}$ values of 0.88 mg/kg against *P. chabaudi* AS. Table 7 shows the efficacy of some of these compounds in three different models of rodent malaria including *P. chabaudi* ASP and the lethal *P. berghei* ANKA. Compared to pyrimethamine which is 15 times less efficacious against pyrimethamine resistant *P. chabaudi* ASP ($ED_{90}$=13.5 mg/kg), compound P113 retains its efficacy against this strain ($ED_{90}$=0.01 mg/kg) and against the lethal *P. berghei* ANKA ($ED_{90}$=0.03 mg/kg).

TABLE 6

Anti-malarial oral activity of compounds against *P. chabaudi* AS in the standard 4-day Peters' Test.

| | *P. chabaudi* AS(mg/kg) | |
|---|---|---|
| Compound Number | $ED_{50}$* | $ED_{90}$* |
| P65 | 0.9 | 1.5 |
| P111 | 0.03 | 7.3 |
| P113 | 0.006 | 0.01 |
| P112 (99.9% inhibition at 30 mg/kg) | nd | nd |
| P134 | 0.025 | 0.076 |
| P135 | 2 | 5.2 |
| P136 | 0.3 | 3.4 |
| P138 | 0.7 | 1.3 |
| P139 | 0.8 | 2.8 |
| P140 (99.9% inhibition at 30 mg/kg) | nd | nd |
| P141 | 0.06 | 0.65 |
| P142 (97.9% inhibition at 30 mg/kg) | nd | nd |
| P144 | 0.54 | 3.08 |
| P145 | 0.03 | 0.12 |
| P146 | 3.8 | 28.8 |
| P147 | 1.96 | 11.8 |
| P148 | 2.21 | 14.1 |
| P149 | 0.01 | 0.02 |
| P153 | 0.006 | 0.013 |
| P154 | 0.006 | 0.043 |
| P155 (99.9% inhibition at 30 mg/kg) | nd | nd |
| P156 | 0.14 | 0.36 |
| P157 | 0.008 | 0.012 |
| P163 | 0.17 | 1.4 |
| P164 | 0.03 | 0.08 |
| P165 | 0.39 | 2.33 |
| P166 | 1.78 | 9.57 |
| P167 (48.3% inhibition at 30 mg/kg) | nd | nd |
| P168 (48.3% inhibition at 30 mg/kg) | nd | nd |
| P169 | >29 | >29 |
| P170 (48.3% inhibition at 30 mg/kg) | nd | nd |
| P171 | 0.16 | 0.9 |
| P172 | 0.22 | 1.74 |
| P173 | >10 | >10 |
| P195 | 0.21 | 0.69 |
| P217 | <0.63 | <0.63 |
| P218 | <0.63 | <0.63 |
| P219 | >5 | >5 |
| Pyrimethamine | 0.25 | 0.88 |

*$ED_{50/90}$: dose required to produce a 50%/90% reduction in parasitaemia.
nd = not determined

TABLE 7

Summary of oral anti-malarial activity of compounds against different rodent malaria models.

|  | P. chabaudi AS (mg/kg) | | P. chabaudi ASP (mg/kg) | | P. berghei ANKA (mg/kg) | |
|---|---|---|---|---|---|---|
|  | $ED_{50}$* | $ED_{90}$* | $ED_{50}$ | $ED_{90}$ | $ED_{50}$ | $ED_{90}$ |
| P65 | 0.9 | 1.5 | 0.7 | 1.5 | 1.4 | 18 |
| P113 | 0.006 | 0.01 | 0.003 | 0.01 | 0.01 | 0.03 |
| P111 | 0.03 | 7.3 | nt | nt | nt | nt |
| P135 | 2.0 | 5.2 | nt | nt | nt | nt |
| P195 | 0.21 | 0.69 | nt | nt | nt | nt |
| P217 | <0.63 | <0.63 | nt | nt | nt | nt |
| P218 | <0.63 | <0.63 | nt | nt | nt | nt |
| Pyrimethamine | 0.25 | 0.88 | 1.8 | 13.5 | 0.5 | 3.2 |

*$ED_{50/90}$: dose required to produce a 50%/90% reduction in parasitaemia.
nt = not tested

Example 16

Bioavailability

To assess the oral bioavailability and pharmacokinetics, test compounds were administered to fasted male Sprague Dawley rats weighing 270-300 g (see Table 8 below). Rats had free access to water throughout the pre- and post-dose sampling period, and access to food was re-instated 4 hours post-dosing. Test compounds were administered intravenously as a 5 minute constant rate infusion (1.0 mL per rat) and orally by gavage (1.0 mL per rat). The IV formulations were typically buffered aqueous solutions containing a co-solvent if required for solubilization. The oral formulations were prepared as suspensions in hydroxypropylmethyl cellulose or carboxymethyl cellulose, each with the addition of Tween 80 and benzyl alcohol. Samples of arterial blood and total urine were collected up to 24 hours post-dose. Arterial blood was collected directly into borosilicate vials (at 4° C.) containing heparin, a protease inhibitor cocktail, potassium fluoride, and EDTA to minimise the potential for ex vivo degradation of the test compound in blood/plasma samples. Once collected, blood samples were centrifuged, supernatant plasma was removed and stored at −20° C., and plasma concentrations of test compound were determined by LCMS.

TABLE 8

Pharmacokinetic parameters for selected compounds determined following i.v. and oral dosing to male Sprague Dawley rats.

| Compound | i.v. $CL_{(plasma)}$ (mL/min/kg) | i.v. $t_{1/2}$ (h) | $V_D$ (L/kg) | Oral BA (% of dose) |
|---|---|---|---|---|
| P111 | 51.4 | 1.7 | 7.4 | 18.5 |
| P113 | Not defined. | Not defined | Not defined | <2.0 |
| P134 | Not defined | Not defined | Not defined | 14.6 |
| P135 | 49.1 | Not defined | 1.6 | 7.0 |
| P149 | 66.3 | 24.3 | 51.2 | 10 |
| P153 | 69.6 | 15.7 | 17.3 | 26 |
| P154 | 84.1 | 3.2 | 8.8 | 9.3 |
| P157 | 74.7 | 17.6 | 15.2 | 25.5 |
| P164 | 218.3 | 0.6 | 11.6 | 1.0 |

The data in Table 8 shows the different pharmacokinetic profiles and bioavailability properties of the various compounds. There is a range of values in terms of oral bioavailability, clearance, $t_{1/2}$ and $V_D$ for the individual compounds.

Figure 9:
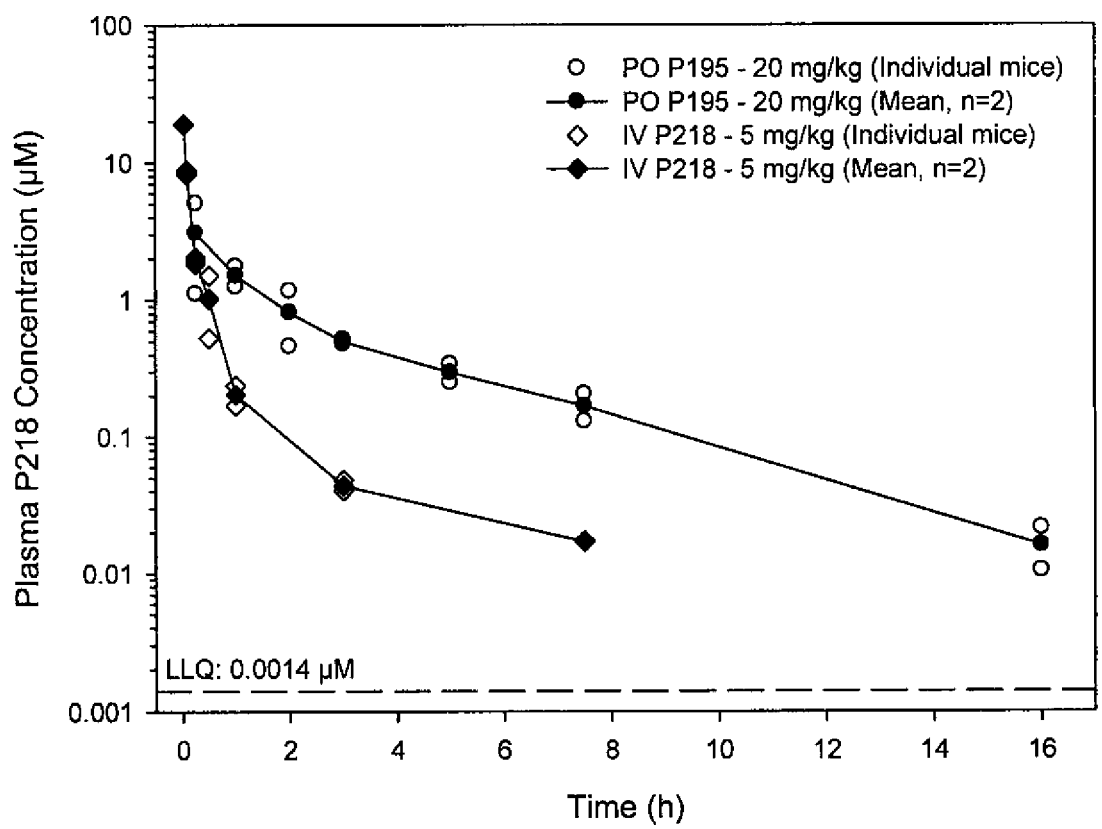
FIG. 9 illustrates the plasma concentrations of P218 in male Swiss Outbred mice following IV administration of P218 (free acid) and oral administration of P195 (ester prodrug).

In a separate study, the oral bioavailability of P195, the ester pro-drug of P218 which contains a carboxylic acid side chain was investigated in mice. Male Swiss outbred mice were administered P218 (the free acid) intravenously by bolus tail vein injection at a nominal dose of 5 mg/kg and P195 (the ester pro-drug) orally by gavage at a nominal dose of 20 mg/kg. Dosing formulations were comparable to those used in the rat studies described above. Blood sampling was conducted by cardiac puncture with a single sample per mouse, and two mice per time point over 16 hours post dosing. Blood samples were separated and plasma analyzed by LCMS as described above. The plasma concentration versus time profiles for P218 following IV administration of P218 and following oral administration of the pro-drug P195 are shown in FIG. 9. Plasma concentrations of P218 remained above the lower limit of quantitation (LLQ=0.0014 μM) for 7.5 h following IV administration. Following oral administration of the ester prodrug, plasma concentration of the acid P218 remained above the LLQ for 16 hours post dosing, and the bioavailability of P218 was approximately 50% (determined by comparison of the dose normalized AUC value for P218 following oral administration of P195 to the AUC for P218 following IV administration of P218). The maximum plasma concentration ($C_{max}$) of P218 following oral administration of P195 was observed at the time of the first blood sample (15 min) and plasma concentrations of the pro-drug P195 were below the lower limit of quantitation (0.0014 μM) at all time points. These results suggest rapid absorption and cleavage of the ester prodrug following oral administration to liberate the acid P218.

Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are understood by those skilled in the art are intended to be within the scope of the claims.

We claim:

1. A compound of Formula I:

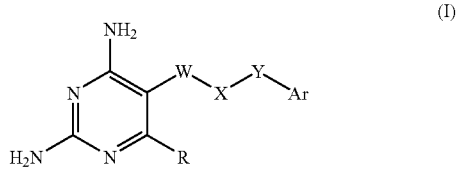

(I)

wherein R is hydrogen or $C_{1-4}$ alkyl,
W—X—Y is $O(CH_2)_{2-4}O$; Ar is an optionally substituted aromatic ring selected from the group consisting of phenyl and naphthyl, or an optionally substituted heteroaromatic ring selected from the group consisting of quinolinyl, isoquinolinyl, quinazolinyl, quinoxalinyl, pyridyl, indolyl, triazolyl, benzoxazolyl, benzimidazolyl, indolinyl and benzotriazolyl; wherein
when Ar is an aromatic ring, it is optionally substituted by at least one group selected from the group consisting of benzoxazolyl, carboxyl, carboxyalkylC(1-3), carboxyalkylC(1-3)oxy, alkylC(1-3)oxycarbonylalkylC(1-3), alkylC(1-3)oxycarbonylalkylC(1-3)oxy, tetrazolyl, tetrazolylalkylC(1-3) and tetrazolylalkylC(1-3)oxy; and Ar is optionally substituted by additional substituents; or a pharmaceutically acceptable salt or substituted derivative thereof.

2. The compound of claim 1, wherein R is $C_{1-4}$ alkyl.

3. The compound of claim 1, wherein R is ethyl.

4. The compound of claim 1, wherein Ar is substituted by at least one group selected from the group consisting of benzoxazolyl, nitro, carboxyl, carboxyalkylC(1-3), carboxyalkylC(1-3)oxy, alkylC(1-3)oxycarbonylalkylC(1-3), alkylC(1-3)oxycarbonylalkylC(1-3)oxy, tetrazolyl, tetrazolylalkylC(1-3) and tetrazolylalkylC(1-3)oxy, Ar is further substituted at one or more available positions with at least one group selected from the group consisting of alkyl, substituted alkyl, cycloalkyl, substituted cycloalkyl, trifluoromethyl, aryl, substituted aryl, halogen, amino, substituted amino, alkoxy, aryloxy, hydroxyl and nitro.

5. The compound of claim 4, wherein Ar is 4-quinolinyl or substituted 4-quinolinyl.

6. The compound of claim 1, wherein R is ethyl, W—X—Y is $O(CH_2)_3O$ and Ar is quinolinyl or substituted 4-quinolinyl.

7. The compound of claim 2, wherein Ar is substituted by at least one group selected from the group consisting of benzoxazolyl, nitro, carboxyl, carboxyalkylC(1-3), carboxyalkylC(1-3)oxy, alkylC(1-3)oxycarbonylalkylC(1-3), alkylC(1-3)oxycarbonylalkylC(1-3)oxy, tetrazolyl, tetrazolylalkylC(1-3) and tetrazolylalkylC(1-3)oxy, Ar is further substituted at one or more available positions with at least one group selected from the group consisting of alkyl, substituted alkyl, cycloalkyl, substituted cycloalkyl, trifluoromethyl, aryl, substituted aryl, halogen, amino, substituted amino, alkoxy, aryloxy, hydroxyl and nitro.

8. The compound of claim 1 wherein said Ar is quinolinyl or substituted 4-quinolinyl.

9. The compound of claim 3, wherein Ar is substituted by at least one group selected from the group consisting of benzoxazolyl, nitro, carboxyl, carboxyalkylC(1-3), carboxyalkylC(1-3)oxy, alkylC(1-3)oxycarbonylalkylC(1-3), alkylC(1-3)oxycarbonylalkylC(1-3)oxy, tetrazolyl, tetrazolylalkylC(1-3) and tetrazolylalkylC(1-3)oxy, Ar is further substituted at one or more available positions with at least one group selected from the group consisting of alkyl, substituted alkyl, cycloalkyl, substituted cycloalkyl, trifluoromethyl, aryl, substituted aryl, halogen, amino, substituted amino, alkoxy, aryloxy, hydroxyl and nitro.

10. The compound of claim 9, wherein said Ar is quinolinyl or substituted 4-quinolinyl.

11. The compound of claim 4, wherein W-X-Y is $O(XCH_2)_{2-4}O$.

12. The compound of claim 1, wherein said compound is is the following compound or a pharmaceutically acceptable salt thereof of the following compound:

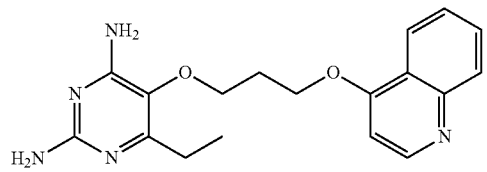 [SMILES: CCc1nc(N)nc(N)c1OCCCOc1ccnc2ccccc12]

2,4-diamino-6-ethyl-5-(3-(quinolin-4-yloxy)propoxy)pyrimidine.

13. The compound of claim 1, wherein said compound is the following compound, or a pharmaceutically acceptable salt thereof of the following compound:

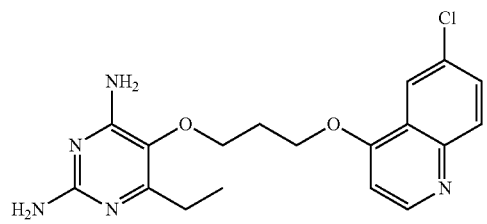

2,4-diamino-6-ethyl-5-(3-(6-chloro-quinolin-4-yloxy)propoxy)pyrimidine.

14. The compound of claim 1, wherein said compound is as follows, or a pharmaceutically acceptable salt thereof of the following compound:

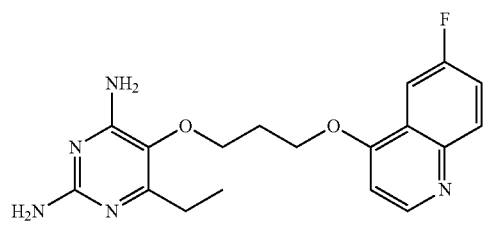 [SMILES: CCc1nc(N)nc(N)c1OCCCOc1ccnc2ccc(Cl)cc12]

2,4-diamino-6-ethyl-5-(3-(6-fluoro-quinolin-4-yloxy)propoxy)pyrimidine.

15. The compound of claim 1, wherein said compound is the following compound, or a pharmaceutically acceptable salt thereof of the following compound:

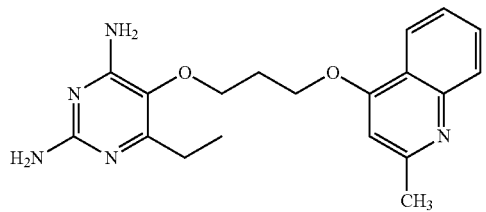 [SMILES: CCc1nc(N)nc(N)c1OCCCOc1cc(C)nc2ccccc12]

2,4-diamino-6-ethyl-5-(3-(2-methylquinolin-4-yloxy)propoxy)pyrimidine.

16. The compound of claim 1, wherein said compound is the following compound, or a pharmaceutically acceptable salt thereof of the following compound:

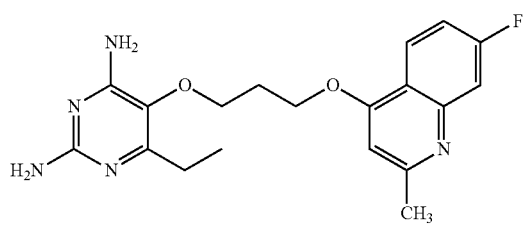 [SMILES: CCc1nc(N)nc(N)c1OCCCOc1cc(C)nc2cc(F)ccc12]

2,4-diamino-6-ethyl-5-(3-(7-fluoro-2-methylquinolin-4-yloxy)propoxy)pyrimidine.

17. The compound of claim 1, wherein said compound is the following compound, or a pharmaceutically acceptable salt thereof of the following compound:

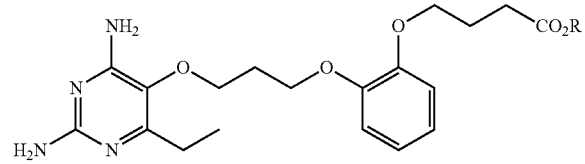

2,4-diamino-6-ethyl-5-(3-(2-(3-carboxypropoxy)phenoxy)propoxy)pyrimidine, wherein R is H.

18. The compound of claim 1, wherein said compound is the following compound or a pharmaceutically acceptable salt thereof of the following compound:

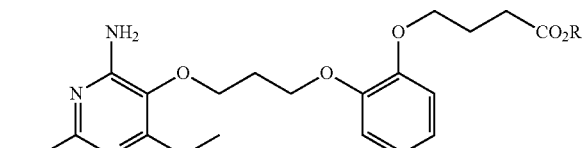

2,4-diamino-6-ethyl-5-(3-(2-(3-carboxypropoxy)phenoxy)propoxy)pyrimidine ethyl ester, wherein R is Et.

19. The compound of claim 1, wherein said compound is the following compound, or a pharmaceutically acceptable salt thereof:

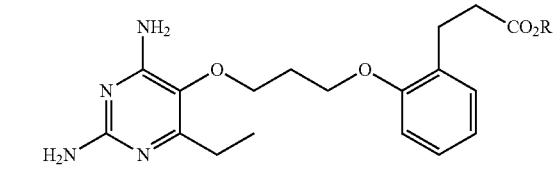

2,4-diamino-6-ethyl-5-(3-(2-(2-carboxyethyl)phenoxy)propoxy)pyrimidine ethyl ester, wherein R is Et.

20. The compound of claim 1, wherein said compound is the following compound, or a pharmaceutically acceptable salt thereof of the following compound:

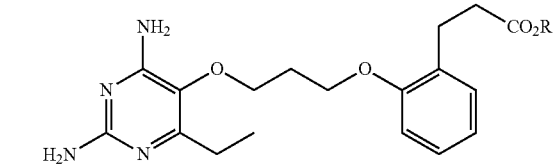

2,4-diamino-6-ethyl-5-(3-(2-(2-carboxyethyl)phenoxy)propoxy)pyrimidine, wherein R is H.

21. The compound of claim 1, wherein said compound is the following compound, or a pharmaceutically acceptable salt thereof of the following compound:

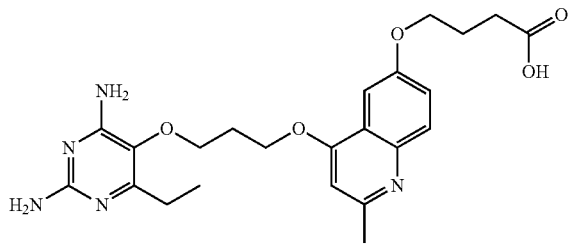 [SMILES: CCc1nc(N)nc(N)c1OCCCOc1cc(C)nc2ccc(OCCCC(=O)O)cc12]

2,4-diamino-6-ethyl-5-(3-(6-(3-carboxypropoxy)-2-methylquinolin-4-yloxy)-propoxy)pyrimidine.

22. The compound of claim 1, wherein said compound is the following compound, or a pharmaceutically acceptable salt thereof of the following compound:

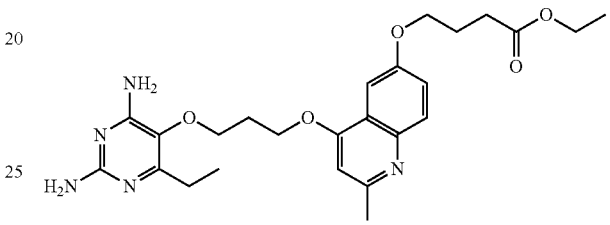

2,4-diamino-6-ethyl-5-(3-(6-(3-carboxypropoxy)-2-methylquinolin-4-yloxy)-propoxy)pyrimidin ethyl ester.

23. The compound according to claim 20, wherein the compound is a pharmaceutically acceptable hydrochloride salt of the following compound:

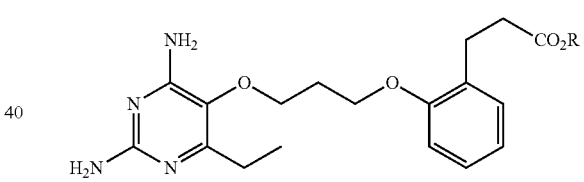

2,4-diamino-6-ethyl-5-(3-(2-(2-carboxyethyl)phenoxy) propoxy)pyrimidine, wherein R is H.

24. A pharmaceutical formulation comprising a compound of Formula (I):

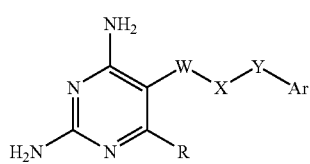

(I)

wherein R is hydrogen or $C_{1-4}$ alkyl,
W—X—Y is $O(CH_2)_{2-4}O$;
Ar is an optionally substituted aromatic ring selected from phenyl and naphthyl, or an optionally substituted heteroaromatic ring selected from the group consisting of quinolinyl, isoquinolinyl, quinazolinyl, quinoxalinyl, pyridyl, indolyl, triazolyl, benzoxazolyl, benzimidazolyl, indolinyl and benzotriazolyl; wherein
when Ar is an aromatic ring, it is substituted by at least one group selected from the group consisting of benzoxazolyl, carboxyl, carboxyalkylC(1-3), carboxyalkylC(1-3)oxy, alkylC(1-3)oxycarbonylalkylC(1-3), alkylC(1-3)oxycarbonylalkylC(1-3)oxy, tetrazolyl, tetrazolylalkylC(1-3) and tetrazolylalkylC(1-3)oxy; and Ar is optionally substituted by additional substituents; or a pharmaceutically acceptable salt or substituted derivative thereof.

25. The pharmaceutical formulation according to claim 24, wherein said compound is the following compound or a pharmaceutically acceptable hydrochloric acid salt thereof:

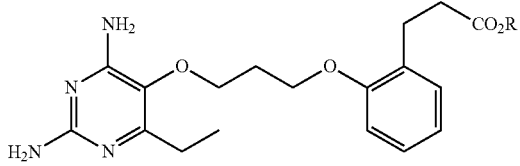

2,4-diamino-6-ethyl-5-(3-(2-(2-carboxyethyl)phenoxy)propoxy)pyrimidine, wherein R is H.

26. A method of synthesis, comprising the steps of: alkylating ArOH according to Scheme 1, Scheme 1

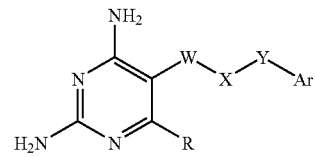

wherein LG is a suitable leaving group and wherein said alkylation step is a step in the method of synthesizing of compounds of Formula (I):

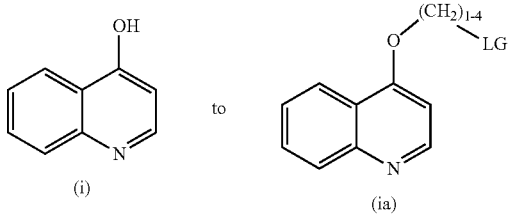

wherein R is hydrogen or $C_{1-4}$ alkyl,
W is O or $CH_2$,
X is $(CH_2)_{2-4}$ and is optionally substituted with a hydroxyl group,
Y is $CH_2$, O, S, N(Z), wherein Z is H, acyl, alkyl, or aryl;
Ar is a substituted aromatic ring comprising phenyl or naphthyl, or an optionally substituted heteroaromatic ring selected from the group consisting of quinolinyl, isoquinolinyl, quinazolinyl, quinoxalinyl, pyridyl, indolyl, triazolyl, benzoxazolyl, benzimidazolyl, indolinyl and benzotriazolyl; and wherein when Ar is an aromatic ring, it is substituted by at least one group selected from the group consisting of acyl, benzoxazolyl, nitro, carboxyl, carboxyalkylC(1-3), carboxyalkylC(1-3)oxy, alkylC(1-3)oxycarbonylalkylC(1-3), alkylC(1-3)oxycarbonylalkylC(1-3)oxy, tetrazolyl, tetrazolylalkylC(1-3) and tetrazolylalkylC(1-3)oxy; and Ar is optionally substituted by additional substituents; or a pharmaceutically acceptable salt or substituted derivative thereof.

27. The method of synthesis according to claim 26, wherein the alkylating step includes alkylating Ar according to Scheme 2, Scheme 2

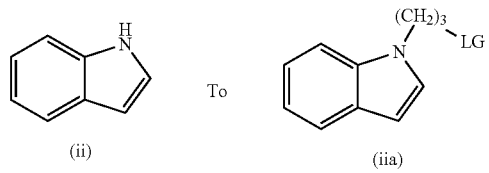

wherein LG is a suitable leaving group and wherein said alkylation step is a step in the method of synthesizing of compounds of Formula (I):

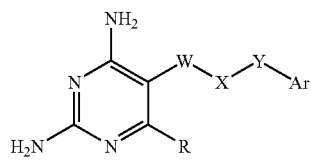

wherein R is hydrogen or $C_{1-4}$ alkyl,
W is O or $CH_2$,
X is $(CH_2)_{2-4}$ and is optionally substituted with a hydroxyl group,
Y is $CH_2$, O, S, N(Z), wherein Z is H, acyl, alkyl, or aryl;
Ar is a substituted aromatic ring comprising phenyl or naphthyl, or an optionally substituted heteroaromatic ring selected from the group consisting of quinolinyl, isoquinolinyl, quinazolinyl, quinoxalinyl, pyridyl, indolyl, triazolyl, benzoxazolyl, benzimidazolyl, indolinyl and benzotriazolyl; and wherein when Ar is an aromatic ring, it is substituted by at least one group selected from the group consisting of acyl, benzoxazolyl, nitro, carboxyl, carboxyalkylC(1-3), carboxyalkylC(1-3)oxy, alkylC(1-3)oxycarbonylalkylC(1-3), alkylC(1-3)oxycarbonylalkylC(1-3)oxy, tetrazolyl, tetrazolylalkylC(1-3) and tetrazolylalkylC(1-3)oxy; and Ar is optionally substituted by additional substituents; or a pharmaceutically acceptable salt or substituted derivative thereof.

28. A method to treat a subject in need of treatment for malaria, which method comprises administering to said subject an effective amount of a compound of claim 1.

29. The method of claim 28, wherein the subject is a subject in need of treatment for a drug-resistant or non-resistant strain of malaria.

30. The method of claim 29, wherein the drug-resistant strain of malaria is a strain that is resistant to at least one antifolate drug.

31. The method of claim 30, wherein the drug-resistant strain of malaria is resistant to at least one antifolate drug selected from the group consisting of cycloguanil, chlorcycloguanil, pyrimethamine or other DHFR inhibitors.

32. The method of claim 30, wherein the drug-resistant strain of malaria is an antifolate-resistant strain having one or more mutations in its DHFR protein sequence.

33. The method of claim 32, wherein the antifolate-resistant strain of malaria has at least two mutations selected from the group consisting of 16(ala to val), 51(asn to ile), 59(cys to arg), 108(ser to asn), 108(ser to thr), and 164(ile to leu).

34. The method of claim 32, wherein the antifolate-resistant strain of malaria has at least one mutation selected from the group consisting of 16(ala to val), 51(asn to ile), 59(cys to arg), 108(ser to asn), 108(ser to thr), and 164(ile to leu).

35. The method of claim 32, wherein the antifolate-resistant strain of malaria has at least one mutation selected from the group consisting of 16(ala to val) and 108(ser to thr).

36. The method of claim 28, wherein the treatment is an oral treatment.

* * * * *

UNITED STATES PATENT AND TRADEMARK OFFICE
CERTIFICATE OF CORRECTION

| | | |
|---|---|---|
| PATENT NO. | : 8,530,491 B2 | Page 1 of 2 |
| APPLICATION NO. | : 12/247953 | |
| DATED | : September 10, 2013 | |
| INVENTOR(S) | : Y. Yuthavong et al. | |

It is certified that error appears in the above-identified patent and that said Letters Patent is hereby corrected as shown below:

Title Page, below abstract, delete "36 Claims, 9 Drawing Sheets" and insert --35 Claims, 9 Drawing Sheets--.

In the Claims
Column 33, lines 47-48, deleted claim 11 in its entirety.
Column 33, line 49, "12." should read --11.--.
Column 33, line 65, "13." should read --12.--.
Column 34, line 15, "14." should read --13.--.
Column 34, line 33, "15." should read --14.--.
Column 34, line 50, "16." should read --15.--.
Column 35, line 1, "17." should read --16.--.
Column 35, line 17, "18." should read --17.--.
Column 35, line 34, "19." should read --18.--.
Column 35, line 50, "20." should read --19.--.
Column 35, line 65, "21." should read --20.--.
Column 36, line 15, "22." should read --21.--.
Column 36, line 31, "23." should read --22.-- and change the dependency from claim 20 to claim 19.
Column 36, line 47, "24." should read --23.--.
Column 37, line 8, "25." should read --24.-- and change the dependency from claim 24 to claim 23.
Column 37, line 23, "26." should read --25.--.
Column 38, line 4, "27." should read --26.-- and change the dependency from claim 26 to claim 25.
Column 38, line 52, "28." should read --27.--.
Column 38, line 55, "29." should read --28.-- and change the dependency from claim 28 to claim 27.
Column 38, line 58, "30." should read --29.-- and change the dependency from claim 29 to claim 28.
Column 38, line 61, "31." should read --30.-- and change the dependency from claim 30 to claim 29.
Column 38, line 65, "32." should read --31.-- and change the dependency from claim 30 to claim 29.
Column 39, line 1, "33." should read --32.-- and change the dependency from claim 32 to claim 31.
Column 39, line 5, "34." should read --33.-- and change the dependency from claim 32 to claim 31.

Signed and Sealed this
Twelfth Day of May, 2015

Michelle K. Lee
*Director of the United States Patent and Trademark Office*

Column 39, line 11, "35." should read --34.-- and change the dependency from claim 32 to claim 31.
Column 39, line 12, "36." should read --35.-- and change the dependency from claim 28 to claim 27.